US012208183B2

(12) United States Patent
Henley

(10) Patent No.: US 12,208,183 B2
(45) Date of Patent: Jan. 28, 2025

(54) ELECTRO-IONIC DEVICES FOR IMPROVED PROTECTION FROM AIRBORNE BIOPATHOGENS

(71) Applicant: Julian Henley, New Orleans, LA (US)

(72) Inventor: Julian Henley, New Orleans, LA (US)

( * ) Notice: Subject to any disclaimer, the term of this patent is extended or adjusted under 35 U.S.C. 154(b) by 0 days.

(21) Appl. No.: 17/911,374

(22) PCT Filed: Mar. 15, 2021

(86) PCT No.: PCT/US2021/022392
§ 371 (c)(1),
(2) Date: Sep. 13, 2022

(87) PCT Pub. No.: WO2021/184012
PCT Pub. Date: Sep. 16, 2021

(65) Prior Publication Data

US 2023/0094157 A1 Mar. 30, 2023

Related U.S. Application Data

(60) Provisional application No. 63/113,598, filed on Nov. 13, 2020, provisional application No. 63/063,968, (Continued)

(51) Int. Cl.
*A61L 9/16* (2006.01)
*A61L 9/04* (2006.01)
(Continued)

(52) U.S. Cl.
CPC ................ *A61L 9/16* (2013.01); *A61L 9/046* (2013.01); *A61L 9/12* (2013.01); *A62B 7/10* (2013.01);
(Continued)

(58) Field of Classification Search
CPC .......... B03C 3/017; B03C 3/155; B03C 3/41; B03C 3/47; B03C 2201/04;
(Continued)

(56) References Cited

U.S. PATENT DOCUMENTS 2,729,302 A * 1/1956 True ........................ B03C 3/155 55/484
3,438,180 A * 4/1969 Klouda .................. B03C 3/155 55/318
(Continued)

FOREIGN PATENT DOCUMENTS

CN 103585844 B 6/2015
CN 109061707 A 12/2018
(Continued)

OTHER PUBLICATIONS

International Searching Authority, International Search Report and Written Opinion, issued in connection with International Application No. PCT/US2021/022392, mailed Jul. 28, 2021 (11 pages).
(Continued)

*Primary Examiner* — Christopher P Jones
*Assistant Examiner* — Sonji Turner
(74) *Attorney, Agent, or Firm* — Polsinelli PC

(57) ABSTRACT

An electro-ionic device that includes an outer frame, a first conductor, an insulating frame, and a second conductor. The outer frame defines a passageway there through. The first conductor is positioned within the outer frame and includes at least one wire configured to be supplied with a voltage. The insulating frame is positioned within outer frame and forms a non-conductive barrier between the first conductor and the outer frame. The second conductor is positioned within and contacts the outer frame.

22 Claims, 14 Drawing Sheets

Related U.S. Application Data filed on Aug. 11, 2020, provisional application No. 63/044,768, filed on Jun. 26, 2020, provisional application No. 63/043,424, filed on Jun. 24, 2020, provisional application No. 63/027,746, filed on May 20, 2020, provisional application No. 62/988,991, filed on Mar. 13, 2020.

(51) Int. Cl.

| | |
|---|---|
| ***A61L 9/12*** | (2006.01) |
| ***A62B 7/10*** | (2006.01) |
| ***B03C 3/017*** | (2006.01) |
| ***B03C 3/155*** | (2006.01) |
| ***B03C 3/41*** | (2006.01) |
| ***B03C 3/47*** | (2006.01) |
| ***F24F 3/16*** | (2021.01) |
| ***F24F 8/30*** | (2021.01) |
| ***F24F 8/40*** | (2021.01) |
| ***F24F 8/80*** | (2021.01) |

(52) U.S. Cl.

CPC .............. *B03C 3/017* (2013.01); *B03C 3/155* (2013.01); *B03C 3/41* (2013.01); *B03C 3/47* (2013.01); *F24F 3/16* (2013.01); *F24F 8/30* (2021.01); *F24F 8/40* (2021.01); *F24F 8/80* (2021.01); *A61L 2209/111* (2013.01); *A61L 2209/14* (2013.01); *A61L 2209/16* (2013.01); *B03C 2201/04* (2013.01); *B03C 2201/08* (2013.01); *F24F 2221/34* (2013.01)

(58) Field of Classification Search

CPC ............ B03C 2201/08; B03C 2201/06; B03C 2201/10; A61L 9/16; A61L 9/046; A61L 9/12; A61L 2209/111; A61L 2209/14; A61L 2209/16; A62B 7/10; A62C 3/14; F24F 3/16; F24F 8/30; F24F 8/40; F24F 8/80; F24F 8/108; F24F 2221/34; F24F 2221/54

See application file for complete search history.

(56) References Cited

U.S. PATENT DOCUMENTS 3,626,668 A * 12/1971 Cardiff .................... B03C 3/155 55/318
3,977,467 A * 8/1976 Northrup, Jr. ........ F24H 3/0405 165/137
4,502,872 A * 3/1985 Ivester ...................... B03C 3/41 96/90
5,368,816 A * 11/1994 Detzer ...................... F24F 8/26 422/4
5,447,763 A 9/1995 Gehlke
5,573,577 A * 11/1996 Joannou .................. B03C 3/155 96/96
5,578,112 A * 11/1996 Krause ...................... B03C 3/41 96/92
5,648,046 A * 7/1997 Weibel ...................... F24F 8/24 422/123
5,788,930 A * 8/1998 McMurray ................ A61L 2/28 422/123
5,820,828 A * 10/1998 Ferone ...................... A61L 9/12 422/112
5,887,439 A 3/1999 Kotliar
5,919,847 A 7/1999 Rousseau et al.
5,924,419 A 7/1999 Kotliar
5,964,222 A 10/1999 Kotliar
5,968,635 A 10/1999 Rousseau et al.
5,976,208 A 11/1999 Rousseau et al.
5,988,161 A 11/1999 Kroll
6,002,017 A 12/1999 Rousseau et al.
6,019,949 A * 2/2000 Dunder ................. C01B 13/115 422/186.07
6,029,664 A 2/2000 Zdrojkowski et al.
6,042,637 A 3/2000 Weinberg
6,056,808 A * 5/2000 Krause ...................... B03C 3/86 96/92
6,073,627 A 6/2000 Sunnen
6,117,176 A 9/2000 Chen
6,119,691 A 9/2000 Angadjivand et al.
6,162,535 A 12/2000 Turkevich et al.
6,192,911 B1 2/2001 Barnes
6,213,122 B1 4/2001 Rousseau et al.
6,214,094 B1 4/2001 Rousseau et al.
6,237,595 B1 5/2001 Rousseau et al.
6,238,466 B1 5/2001 Rousseau et al.
6,240,933 B1 6/2001 Bergman
6,261,342 B1 7/2001 Rousseau et al.
6,267,125 B1 7/2001 Bergman et al.
6,268,495 B1 7/2001 Rousseau et al.
6,273,108 B1 8/2001 Bergman et al.
6,281,515 B1 8/2001 Demeo et al.
6,305,374 B1 10/2001 Zdrojkowski et al.
6,314,754 B1 11/2001 Kotliar
6,324,703 B1 12/2001 Chen
6,333,374 B1 12/2001 Chen
6,334,315 B1 1/2002 Kotliar
6,365,103 B1 4/2002 Fournier
6,375,714 B1 * 4/2002 Rump ..................... F24F 8/192 96/96
6,375,886 B1 4/2002 Angadjivand et al.
6,401,487 B1 6/2002 Kotliar
6,405,387 B1 6/2002 Barnes
6,406,657 B1 6/2002 Eitzman et al.
6,426,053 B1 7/2002 Barnes
6,428,756 B1 8/2002 Barnes
6,432,077 B1 8/2002 Stenzler
6,432,367 B1 * 8/2002 Munk .................... B01D 47/06 422/171
6,488,634 B1 12/2002 Rapoport et al.
6,502,421 B2 1/2003 Kotliar
6,539,940 B2 4/2003 Zdrojkowski et al.
6,557,374 B2 5/2003 Kotliar
6,560,991 B1 5/2003 Kotliar
6,561,185 B1 5/2003 Kroll
6,582,525 B2 6/2003 Bergman
6,591,845 B1 7/2003 Bergman et al.
6,601,594 B2 8/2003 Bergman et al.
6,614,505 B2 9/2003 Koster et al.
6,623,635 B2 9/2003 Barnes
6,627,563 B1 9/2003 Huberty
6,629,527 B1 10/2003 Estes et al.
6,701,941 B1 3/2004 Bergman et al.
6,745,764 B2 6/2004 Hickle
6,776,951 B2 8/2004 Rousseau et al.
6,793,644 B2 9/2004 Stenzler
6,807,965 B1 10/2004 Hickle
6,817,370 B2 11/2004 Bergman et al.
6,820,619 B2 11/2004 Kroll
6,828,578 B2 12/2004 DeMeo et al.
6,830,628 B2 12/2004 Bergman
6,837,252 B2 1/2005 Bergman
6,841,791 B2 1/2005 DeMeo et al.
6,843,857 B2 1/2005 Bergman
6,854,135 B2 2/2005 Jones et al.
6,862,075 B2 3/2005 Koster et al.
6,867,253 B1 3/2005 Chen
6,869,487 B1 3/2005 Bergman
6,901,930 B2 6/2005 Henley
6,948,497 B2 9/2005 Zdrojkowski et al.
6,986,347 B2 1/2006 Hickle
6,991,532 B2 * 1/2006 Goldsmith ............. B01D 53/72 454/157
6,997,180 B2 2/2006 Kroll
7,008,465 B2 3/2006 Graham et al.
7,013,892 B2 3/2006 Estes et al.
7,025,869 B2 4/2006 Fine et al.
7,028,689 B2 4/2006 Martin et al.
7,040,313 B2 5/2006 Fine et al.
7,047,970 B2 5/2006 Umeda et al.

(56) References Cited

U.S. PATENT DOCUMENTS 7,122,018 B2 10/2006 Stenzler et al.
7,135,108 B1 11/2006 Barnes
7,148,085 B2 12/2006 Abbott et al.
7,201,734 B2 4/2007 Hickle
7,203,974 B2 4/2007 Jones et al.
7,244,291 B2 7/2007 Spartz et al.
7,244,292 B2 7/2007 Kirk et al.
7,247,154 B2 7/2007 Hickle
7,308,894 B2 12/2007 Hickle
RE40,065 E 2/2008 Kotliar
7,332,019 B2 * 2/2008 Bias .......................... B03C 3/72 96/26
7,334,580 B2 2/2008 Smaldone et al.
7,335,181 B2 2/2008 Miller et al.
7,351,274 B2 * 4/2008 Helt ........................ B03C 3/155 96/26
7,390,351 B2 6/2008 Leir et al.
7,520,866 B2 4/2009 Stenzler et al.
7,564,201 B2 * 7/2009 Steckling ................ A61L 9/015 315/307
7,578,997 B2 8/2009 MacDonald
7,601,204 B2 * 10/2009 Woodruff ................ B03C 3/017 96/81
7,607,436 B2 10/2009 Smaldone et al.
7,647,927 B2 1/2010 Teezel et al.
7,658,891 B1 2/2010 Barnes
7,765,698 B2 8/2010 Sebastian et al.
7,802,572 B2 9/2010 Hahne
7,887,889 B2 2/2011 David et al.
7,892,198 B2 2/2011 Stenzler
7,909,918 B2 * 3/2011 Bias .......................... B03C 3/86 96/81
7,931,733 B2 4/2011 Kotliar
7,955,418 B2 6/2011 Claussen et al.
7,975,692 B2 7/2011 Eifler et al.
7,976,855 B2 7/2011 MacDonald et al.
7,992,556 B2 8/2011 Hickle
8,015,970 B2 9/2011 Klun et al.
8,043,252 B2 10/2011 Miller et al.
8,062,411 B2 11/2011 Blucher et al.
8,066,904 B2 11/2011 Fine et al.
8,067,110 B2 11/2011 Rakow
8,072,291 B2 12/2011 Itoh et al.
8,113,198 B2 2/2012 Teetzel et al.
8,182,800 B2 5/2012 MacDonald
8,221,800 B2 7/2012 Fine et al.
8,245,708 B2 8/2012 Smaldone et al.
8,261,747 B2 9/2012 Smaldone et al.
8,292,991 B2 10/2012 Friday et al.
8,298,320 B2 10/2012 Cozean
8,303,693 B2 11/2012 Leung
8,318,084 B2 * 11/2012 Johnson ............. B01D 53/8675 422/123
8,334,524 B2 12/2012 DeMeo et al.
8,356,594 B2 1/2013 Ujhazy et al.
8,366,816 B2 2/2013 Bohringer et al.
8,371,296 B2 2/2013 Fine et al.
8,388,731 B2 * 3/2013 Metteer .................. B01D 53/32 422/123
8,397,715 B2 3/2013 Litz
8,416,033 B2 4/2013 Itoh et al.
8,480,797 B2 7/2013 Cozean et al.
8,585,808 B2 11/2013 Croll et al.
8,602,023 B2 12/2013 Smaldone et al.
8,613,795 B2 12/2013 Li et al.
8,647,419 B2 2/2014 Kaskel
8,653,979 B2 2/2014 Obenchain
8,667,960 B2 3/2014 Ausen
8,673,061 B2 3/2014 Cozean et al.
8,684,189 B2 4/2014 Chen et al.
8,714,156 B2 5/2014 Cooke et al.
8,733,350 B2 5/2014 Smaldone et al.
8,753,434 B2 6/2014 Croll et al.
8,757,154 B2 6/2014 Schuller
8,763,712 B2 7/2014 Kotliar
8,765,133 B2 7/2014 Tsukamoto
8,776,796 B2 7/2014 Nolan
8,790,449 B2 7/2014 Li et al.
8,795,222 B2 8/2014 Stenzler et al.
8,815,244 B2 8/2014 Tsukamoto
8,845,782 B2 * 9/2014 Metteer ..................... A61L 9/12 95/55
8,859,995 B2 10/2014 Liu et al.
8,882,703 B2 11/2014 Hickle
8,887,719 B2 11/2014 Billingsley et al.
8,887,726 B2 11/2014 Schulz et al.
8,899,227 B2 12/2014 Billingsley et al.
8,944,048 B2 2/2015 Monzyk
8,950,401 B2 2/2015 Teetzel et al.
8,955,515 B2 2/2015 Rakow et al.
8,960,194 B2 2/2015 Cooke et al.
8,967,147 B2 3/2015 Martin
9,011,584 B2 4/2015 Tobias et al.
9,079,049 B2 7/2015 Tobias et al.
9,095,422 B2 8/2015 Gray et al.
9,120,571 B2 9/2015 Kshirsagar et al.
9,127,363 B2 9/2015 David et al.
9,127,691 B2 9/2015 Hagen et al.
9,132,251 B2 9/2015 Johansen
9,132,252 B2 9/2015 Barlow et al.
9,155,923 B2 10/2015 Proctor
9,171,689 B2 10/2015 Liu et al.
9,186,472 B2 11/2015 Cozean et al.
9,192,626 B2 11/2015 Willoughby et al.
9,200,804 B2 12/2015 Park et al.
9,220,858 B2 12/2015 Nolan
9,248,248 B2 2/2016 Virr et al.
9,283,341 B2 3/2016 Ujhazy et al.
9,284,669 B2 3/2016 Li et al.
9,308,492 B2 * 4/2016 Obee .................... B01D 53/346
9,333,378 B2 5/2016 Ishikawa et al.
9,353,966 B2 * 5/2016 Finkam .................... F24F 11/77
9,393,448 B2 7/2016 Dwyer et al.
9,421,515 B2 8/2016 Yoshizaki et al.
9,440,219 B2 9/2016 Bohringer et al.
9,440,775 B2 9/2016 Dwyer et al.
9,457,207 B2 10/2016 Waterford
9,481,424 B2 11/2016 Hagen et al.
9,492,690 B2 11/2016 Hamerly et al.
9,506,173 B2 11/2016 Iwata et al.
9,550,570 B2 1/2017 Kshirsagar et al.
9,580,177 B2 2/2017 Kshirsagar et al.
9,623,404 B2 4/2017 Hupp et al.
9,642,868 B2 5/2017 Wei
9,714,860 B2 7/2017 Obenchain
9,744,328 B2 8/2017 Billingsley et al.
9,744,329 B2 8/2017 Billingsley et al.
9,757,530 B2 9/2017 Nolan
9,802,014 B2 10/2017 Nolan
9,808,655 B2 11/2017 Fromage
9,820,881 B2 11/2017 Aarestad et al.
9,821,291 B2 11/2017 Wood
9,861,774 B2 1/2018 Fu et al.
9,895,382 B2 2/2018 Wei
9,901,128 B2 2/2018 Gray et al.
9,956,232 B2 5/2018 Wei
9,956,371 B2 5/2018 DeVries et al.
9,968,809 B2 5/2018 Ryu et al.
9,998,804 B2 6/2018 Awiszus et al.
10,004,858 B2 6/2018 Smaldone et al.
10,035,128 B2 7/2018 Wood
10,046,134 B2 8/2018 DeVries et al.
10,092,442 B2 10/2018 Aarestad et al.
10,099,072 B2 10/2018 LeVan, Jr. et al.
10,099,165 B2 10/2018 Walls et al.
10,105,509 B2 10/2018 DeVries et al.
10,112,026 B2 10/2018 Schulz et al.
10,130,831 B2 11/2018 Teetzel et al.
10,130,833 B2 11/2018 Angadjivand et al.
10,143,948 B2 12/2018 Bonifas et al.
10,182,946 B2 1/2019 Gray et al.
10,195,217 B2 2/2019 Wei
10,201,198 B2 2/2019 Tong et al.

(56) References Cited

U.S. PATENT DOCUMENTS 10,213,629 B2 2/2019 Tobias
10,238,822 B2 3/2019 Barlow et al.
10,245,406 B2 4/2019 DeVries et al.
10,272,279 B2 4/2019 Hupp et al.
10,315,002 B2 6/2019 DeVries et al.
10,322,303 B2 6/2019 Qian et al.
10,328,625 B2 6/2019 Gray et al.
10,343,000 B2 7/2019 Givens et al.
10,369,320 B2 8/2019 Ahmad et al.
10,387,696 B2 8/2019 Hamerly et al.
10,441,828 B2 10/2019 Curran et al.
10,456,724 B2 10/2019 Huang et al.
10,464,001 B2 11/2019 Kirk et al.
10,485,940 B2 11/2019 Nolan
10,512,429 B2 12/2019 Lau et al.
10,518,059 B2 12/2019 Cipollone et al.
10,537,755 B2 1/2020 Parham et al.
10,542,332 B2 1/2020 Awiszus et al.
10,561,863 B1 2/2020 Dashevsky et al.
10,576,237 B2 3/2020 DeVries et al.
10,610,708 B2 4/2020 Awiszus et al.
10,617,894 B2 4/2020 Nien O et al.
10,625,186 B2 4/2020 Bonifas et al.
10,653,552 B2 5/2020 Aarestad et al.
10,691,908 B2 6/2020 Howard et al.
10,695,521 B2 6/2020 Harrington
10,709,855 B2 7/2020 Nolan
10,722,477 B2 7/2020 Wei
10,744,351 B2 8/2020 Fujimori et al.
10,751,660 B2 8/2020 Legare et al.
10,758,699 B2 9/2020 Cipollone et al.
10,758,751 B2 9/2020 Feasey et al.
10,786,691 B2 9/2020 Kao et al.
10,786,693 B1 9/2020 Opperman et al.
10,814,261 B2 10/2020 Jinka et al.
10,817,683 B2 10/2020 Hamerly et al.
10,821,243 B2 11/2020 Obenchain
10,821,255 B2 11/2020 Zereshkian
10,834,980 B2 11/2020 Magidson et al.
10,849,790 B2 12/2020 Awiszus et al.
10,856,802 B2 12/2020 Ujhazy et al.
10,867,224 B2 12/2020 Howard et al.
10,874,810 B2 12/2020 Fu et al.
10,874,891 B2 12/2020 Biemelt et al.
10,912,961 B2 2/2021 Seo et al.
10,926,114 B2 2/2021 Thompson et al.
10,929,730 B2 2/2021 Shannon et al.
10,932,505 B1 3/2021 Ward et al.
10,946,223 B2 3/2021 Morgan, III et al.
10,953,248 B2 3/2021 Yu et al.
10,960,341 B2 3/2021 Wendland et al.
10,967,207 B2 4/2021 Son et al.
10,981,022 B2 4/2021 Zhao et al.
11,000,827 B2 5/2021 Maanum et al.
11,007,339 B2 5/2021 Reeh et al.
11,007,341 B2 5/2021 Schuller
11,014,070 B2 5/2021 Kobe et al.
11,023,818 B2 6/2021 Awiszus et al.
11,027,236 B2 6/2021 Maayan et al.
11,033,763 B2 6/2021 Nguyen et al.
11,045,787 B2 6/2021 Kobe et al.
11,052,169 B1 7/2021 Pisharodi
11,071,840 B2 7/2021 Reeh et al.
11,077,394 B2 8/2021 Smith
11,083,863 B2 8/2021 Schulz et al.
11,090,515 B2 8/2021 Schuller
11,090,589 B2 8/2021 Bansal et al.
11,103,159 B2 8/2021 Harshman et al.
11,103,822 B2 8/2021 Wendland et al.
11,110,306 B2 9/2021 Montoya et al.
11,123,510 B2 9/2021 Mauger et al.
11,172,845 B1 11/2021 Everman et al.
11,185,655 B2 11/2021 Cipollone et al.
11,213,639 B2 1/2022 Barlow et al.
11,219,788 B2 1/2022 Dwyer et al.
11,235,183 B1 2/2022 Dashevsky et al.
11,247,015 B2 2/2022 DeVries et al.
11,250,303 B2 2/2022 Howard et al.
11,260,251 B2 3/2022 Awiszus et al.
11,273,333 B2 3/2022 Sabolis et al.
11,278,832 B2 3/2022 Jasuja et al.
11,291,255 B2 4/2022 Kanukurthy et al.
11,291,791 B2 4/2022 DeVries et al.
11,300,716 B2 4/2022 Wheatley et al.
11,305,135 B2 4/2022 Givens et al.
11,314,971 B2 4/2022 Ylitalo et al.
11,343,598 B2 5/2022 Awiszus et al.
11,344,692 B2 5/2022 Cipollone et al.
11,354,523 B2 6/2022 Hamerly et al.
11,357,882 B2 6/2022 Dunbar
11,358,014 B2 6/2022 Farmer et al.
11,373,076 B2 6/2022 McCoy et al.
11,375,761 B2 7/2022 Hsien
11,376,451 B2 7/2022 Schuller
11,389,397 B2 7/2022 Wei
11,389,462 B2 7/2022 Wei
11,389,676 B2 7/2022 Schuller
11,406,649 B2 8/2022 Wei
11,452,793 B1 9/2022 Fulbrook
11,559,708 B2 1/2023 Zilberstein et al.
2002/0014401 A1* 2/2002 Fleischer .................. A61L 9/22 422/186.04
2003/0072675 A1* 4/2003 Takeda ...................... A61L 9/22 422/186.04
2004/0041564 A1* 3/2004 Brown .................... F24F 8/192 324/318
2004/0216745 A1 11/2004 Yuen et al.
2004/0262241 A1* 12/2004 Socha ................ B01D 53/8675 422/4
2005/0129571 A1* 6/2005 Centanni ................. A61L 2/202 422/62
2005/0186108 A1* 8/2005 Fields ..................... A61L 2/202 422/123
2005/0207951 A1* 9/2005 Lee ......................... A61L 9/015 422/186.07
2006/0079168 A1* 4/2006 Goldsmith ........... B60H 3/0078 454/156
2006/0104858 A1* 5/2006 Potember ................ A61L 9/205 422/123
2006/0130663 A1* 6/2006 Joshi .................... B01D 53/007 422/186.2
2007/0163588 A1 7/2007 Hebrank
2008/0075639 A1 3/2008 Hooper et al.
2008/0199351 A1* 8/2008 Woodbridge ........... A61L 9/015 422/4
2009/0126382 A1* 5/2009 Rubino ................... F24F 8/192 422/108
2010/0089240 A1* 4/2010 Krichtafovitch .... F24C 15/2035 96/95
2010/0114011 A1 5/2010 Herrmann
2010/0307332 A1 12/2010 Yuen
2011/0087084 A1 4/2011 Jeong et al.
2016/0146483 A1* 5/2016 Sakai ........................ F24F 6/04 261/26
2017/0258150 A1 9/2017 Abdulqader et al.
2017/0354978 A1 12/2017 Krichtafovitch
2018/0064968 A1 3/2018 Taslagyan
2020/0188932 A1* 6/2020 Krichtafovitch ........ F24F 8/192
2021/0322799 A1 10/2021 Pachoud et al.
2021/0330853 A1 10/2021 Mizandari
2021/0346732 A1 11/2021 Tu
2022/0040504 A1 2/2022 Johnston et al.
2022/0330630 A1 10/2022 Vandendorpe et al.
2023/0102633 A1 3/2023 Henley
2024/0001053 A1 1/2024 Henley
2024/0001176 A1 1/2024 Henley
2024/0001375 A1 1/2024 Henley

FOREIGN PATENT DOCUMENTS

EP 1905458 B1 * 11/2018 ............... A61L 9/22
ES 1073677 U 1/2011
GB 2467221 A 7/2010

(56) References Cited

FOREIGN PATENT DOCUMENTS

| | | | | | |
|---|---|---|---|---|---|
| JP | H0975436 | A | * | 3/1997 | |
| JP | 2018136315 | A | | 8/2018 | |
| KR | 101507559 | B1 | | 3/2015 | |
| RU | 201474 | U1 | | 12/2020 | |
| WO | WO 2005/060366 | A2 | | 7/2005 | |
| WO | WO 2005/087320 | A1 | | 9/2005 | |
| WO | WO-2010103296 | A2 | * | 9/2010 | ............. A61L 2/202 |
| WO | WO 2014/082120 | A1 | | 6/2014 | |
| WO | WO 2019/012043 | A1 | | 1/2019 | |
| WO | WO-2020039379 | A1 | * | 2/2020 | |
| WO | WO 2021/207098 | A1 | | 10/2021 | |

OTHER PUBLICATIONS

International Searching Authority, International Search Report and Written Opinion, issued in connection with International Application No. PCT/US2021/022386, mailed Jun. 9, 2021 (11 pages).

International Searching Authority, International Search Report and Written Opinion, issued in connection with International Application No. PCT/US2022/071174, dated Aug. 1, 2022, 20 pgs.

International Searching Authority, International Search Report and Written Opinion, issued in connection with International Application No. PCT/US2022/071169, dated Jul. 26, 2022, 16 pgs.

International Searching Authority, International Search Report and Written Opinion, issued in connection with International Application No. PCT/US2022/071175, dated Jul. 14, 2022, 10 pgs.

Ex Parte Quayle Action, U.S. Appl. No. 18/368,442, dated Nov. 30, 2023, 11 pgs.

Notice of Allowance, U.S. Appl. No. 17/911,372, dated Jan. 23, 2024, 21 pgs.

JP Decision to Grant, JP2023-557073, dated Feb. 1, 2024, 3 pgs. (English machine translation).

Notice of Allowance, U.S. Appl. No. 18/368,442, dated Feb. 16, 2024, 25 pgs.

Extended European Search Report, EP 21768625.2, dated Mar. 21, 2024, 8 pgs.

International Search Report and Written Opinion, issued in connection with International Application No. PCT/US2024/018254, dated Aug. 7, 2024, 24 pgs.

Non-Final Office Action, U.S. Appl. No. 18/438,694, dated Aug. 29, 2024, 30 pgs.

EPO, Extended European Search Report, EP22772374.9, dated Sep. 30, 2024, 11 pgs.

* cited by examiner

ELECTRO-IONIC DEVICES FOR IMPROVED PROTECTION FROM AIRBORNE BIOPATHOGENS

CROSS REFERENCE TO RELATED APPLICATION

This application claims priority from Patent Cooperation Treaty (PCT) Patent Appln. No. PCT/US2021/022392 filed Mar. 15, 2021, which claims benefit of priority under 35 U.S.C. § 119 (e) from U.S. Provisional Patent Appln. No. 62/988,991 filed on Mar. 13, 2020, U.S. Provisional Patent Appln. No. 63/027,746 filed on May 20, 2020, U.S. Provisional Patent Appln. No. 63/043,424 filed on Jun. 24, 2020, U.S. Provisional Patent Appln. No. 63/044,768 filed on Jun. 26, 2020, U.S. Provisional Patent Appln. No. 63/063,968 filed on Aug. 11, 2020, and U.S. Provisional Patent Appln. No. 63/113,598 filed on Nov. 13, 2020, the entirety of each is incorporated by reference herein. This application also incorporates by reference in its entirety U.S. Pat. No. 6,901,930 filed on Oct. 28, 2002.

FIELD OF THE INVENTION

This application relates to devices and methods for improved protection from airborne biopathogens. In particular, this application relates to devices and methods for particle capture and deactivation in a heating, ventilation, and air conditioning (HVAC) system.

BACKGROUND OF THE INVENTION

It is difficult for patients and practitioners to control the transmission of airborne viruses and infections. Examples of such infections include seasonal flu, common colds, and measles, among others. Recently, COVID-19 is thought to have a component of airborne transmission and cross infection. Some researchers believe that under normal circumstances, when small airborne particles enter the lungs, some of them may directly bypass the airway defensive system which is made up of mucous membranes in the nasal and oral cavity as well as the bronchial tree. These particles may enter the distal alveolus where they can rapidly begin contacting cells of the internal organ. Such penetration of the distal alveolus is thought to be confined to the smaller particles as the larger particles are trapped by the body's own filtration system.

Although the exact mechanism of viral transmission remains a point of controversy, some investigators lean towards the fact that viral transmission occurs through touching and then movement of the fingers to enter mucous membranes where the virus can implant itself. This theory is based on the idea that the human cough sprays larger droplets that can be effectively precipitated or filtered and do not necessarily need to be inhaled. The exact mechanism of transmission remains controversial, but some investigators postulate that the small particles penetrating the distant alveolus is a significant modality of transmission. It is quite possible that the salivary droplets and mucous droplets that contain the virus and exit an infected patient as a cough mist partially evaporate or settle onto a surface. Such micro-droplets get smaller via evaporation and may become airborne again in the proximity of the enclosed space or circulating HVAC systems, such as in buildings, automobiles, and airplanes. The airborne transmissibility is predicated on the functional viability of the virus outside of the body in the air, and in the HVAC systems. Recent studies of COVID-19 have demonstrated that the viral particle remains viable in contact with plastic or metal surfaces for extended periods of time, for hours and even days. This is worrisome because it implicates existing ventilation systems with possible spread of COVID-19 virus among other viral, bacterial, or fungal particles.

Given the challenges associated with limiting the transmission of airborne viruses and infections and the desire to reinstate the economic systems, aspects of the present disclosure were developed to provide adequate entrapment of viral particles and droplets, and to provide a virus kill technology in real-time in HVAC systems.

SUMMARY OF THE INVENTION

Aspects of the present disclosure include an electro-ionic device. The device includes an outer frame, a first conductor, an insulating frame, and a second conductor. The outer frame defines a passageway there through. The first conductor is positioned within the outer frame and includes at least one wire configured to be supplied with a voltage. The insulating frame is positioned within outer frame and forms a non-conductive barrier between the first conductor and the outer frame. The second conductor is positioned within and contacts the outer frame.

In certain instances, the device acts as an electrostatic precipitator when negative voltage is applied to the first conductor and when the second conductor is grounded.

In certain instances, the first conductor is arranged in a first plane, and the second conductor is arranged in a second plane, the first and second planes being parallel and spaced apart from each other.

In certain instances, the first conductor is spaced apart from the second conductor between about 1 inch and about 4 inches.

In certain instances, the second conductor is a rectangular screen.

In certain instances, the outer frame includes a four sided structure.

In certain instances, the four sided structure is configured to replace a section of a duct in a heating, ventilation, and air conditioning system.

Aspects of the present disclosure include an electro-ionic device including a base plate, a base platform, a rod, and an emitter assembly. The base platform is coupled to the base plate and includes a first conductor recess formed therein. The base platform is non-conductive. The rod extends through and is movable relative to the base plate and the base platform. The emitter assembly is adjustably coupled to the rod and includes a first conductor. The emitter assembly is configured to transition between a non-deployed state and a deployed state via actuation of the rod, the non-deployed state having the first conductor positioned within the first conductor recess, and the deployed state having the first conductor positioned outside the first conductor recess.

In certain instances, the base plate is configured to be secured to a duct having an opening therein, wherein the platform and emitter assembly are configured to be positioned within the duct when the base plate is secured to the duct.

In certain instances, the first conductor is one of a first plurality of conductors, and the first conductor recess is one of a first plurality of conductor recesses, the emitter assembly further includes a second plurality of conductors, and the base platform further includes a second plurality of conductor recesses.

In certain instances, in the deployed state, the first plurality of conductors and the second plurality of conductors are generally perpendicular to the base plate.

In certain instances, in the deployed state, the first plurality of conductors and the second plurality of conductors are generally parallel with each other.

In certain instances, the first plurality of conductors are coupled to a first plate, and the second plurality of conductors are coupled to a second plate.

In certain instances, the actuation of the rod causes the first plate and the second plate to rotate into a generally parallel orientation.

Aspects of the present disclosure include a system for mitigation of environmental loading of biopathogens. The system includes an electro-ionic device, an ozone generator, a controller, and at least one ozone sensor. The electro-ionic device is in fluid communication with ducts in a heating, ventilation, and air conditioning system and is configured to ionize airflow within the ducts. The first conductor is insulated from contact with the ducts and configured to be supplied with a negative voltage. The ozone generator is in fluid communication with the ducts and configured to deliver ozone into the ducts. The controller is in communication with and configured to control the electro-ionic device and the ozone generator. The at least one ozone sensor is configured to detect levels of ozone in an area, the at least one ozone sensor in communication with the controller.

In certain instances, the electro-ionic device further includes a second conductor in close proximity to a first conductor, the second conductor being grounded to the ducts, the electro-ionic device being an electrostatic precipitator.

In certain instances, the system further includes a humidifier in fluid communication with the ducts and in communication with the controller.

In certain instances, the at least one ozone sensor comprises a first and a second ozone sensor, the first ozone sensor positioned within the ducts, and the second ozone sensor positioned outside the ducts.

In certain instances, the controller is configured to maintain ozone within the ducts to levels within in a biologically safe range.

In certain instances, the controller is configured to decrease an amount of ozone delivered into the ducts by the ozone generator when a threshold value of ozone is exceeded at the at least one ozone sensor.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION

Figure 1:
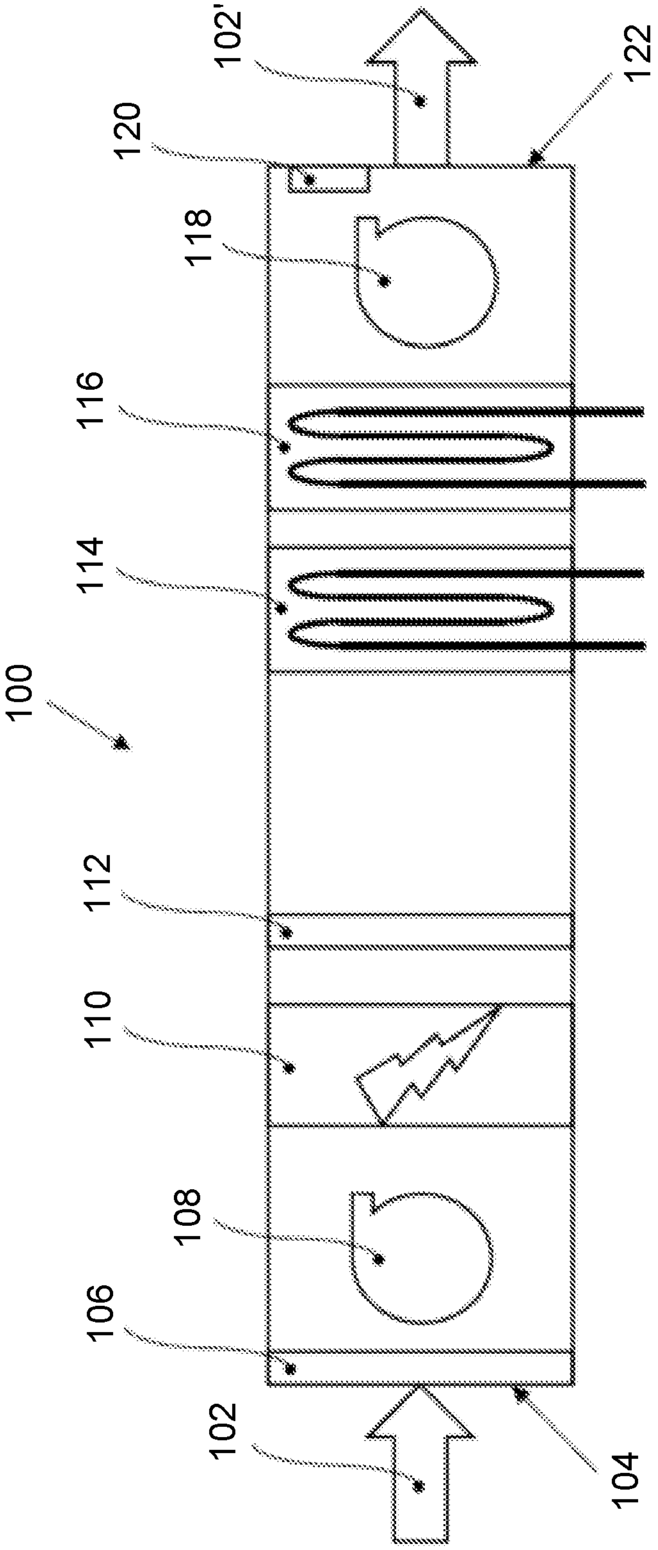
FIG. 1 is a diagrammatic view of an electro-ionic device in an HVAC system according to an exemplary embodiment of the present disclosure.

In an embodiment, as seen in the diagrammatic view of FIG. 1, an electro-ionic device 110 may be incorporated into an HVAC system 100 to mitigate the environmental loading of biopathogens in a given space. A system of this nature may be helpful to mitigate the spread of the COVID-19 virus, among other viruses, bacteria, and fungal particles, and allow for reinstatement of economic systems and return to work with lower risk of infection. The ionization technology described herein can mitigate the external environment in closed spaces such as, for example, office buildings, auditoriums, airplanes, and locations where people congregate to work or interact socially.

In the current understanding of airborne transmission of COVID-19, when people exhale, speak, or cough, they extrude droplets of saliva and mucous, many of which may contain virus particles. These droplets are usually large and can be well mitigated by existing filtration technology. It is over time that these larger droplets evaporate and become smaller, yet still carry viral particles. Some of these droplets may become embedded in masks or filters and then subsequently dislodge to the outside environment or into the lungs. These smaller droplets in the submicron size-range may still carry viable virus into ventilation systems, which have numerous metallic surfaces. It has been found that viruses, such as COVID-19, can thrive for an excess of three days on metallic surfaces. Such particles may become embedded within the HVAC filters and radiators or even trapped on the walls of the ventilation system. It is at least in this area that the electrostatic precipitator is helpful in mitigating the ventilation system from becoming a viral or biopathogen reservoir.

As seen in FIG. 1, the HVAC system 100 may include an inlet fan 108 that circulates inlet air 102 taking it from an intake vent 104 and moving it through the system 100 and out of an output vent 122 as outlet air 102'. The inlet air 102 may encounter a heating coil 114 if heating is required and/or an expansion coil 116 for air-conditioning or dehumidification if such is required. The system 100 may be controlled by a feedback controller, such as a thermostat with on/off timing capability. The thermostat is usually located in a living space and accessible to be manually set. The HVAC systems 100 may be controlled remotely through a wireless interface, such as Wi-Fi or Bluetooth through the Internet. Various parameters of the system may be controlled such as, for example, fan speed, temperature, humidity, and ozone level, etc. as a function of time.

The HVAC system 100 may include one or more fans such as an inlet fan 108 near the inlet 104 and optionally an outlet fan 118 near the outlet 122. The electro-ionic device 110 may be positioned upstream or downstream from the inlet fan 108. The electro-ionic device 110 may be activated from the same circuit as the inlet fan 108. In this instance, the electro-ionic device 110 will not activate unless the inlet fan 108 is activated; therefore, the unit will be powered by the same power supply that powers the inlet fan 108 that drives the air through the HVAC system 100. In another instance, the electro-ionic device 110 may be continually operated without regard to the state of the inlet fan 108. The electro-ionic device 110 may be AC powered or DC powered depending on the particular application.

In certain instances, the electro-ionic device 110 may be retrofitted to existing HVAC systems 100 so the heating coil 114 and the cooling expansion coil 116 remain in place and older flow controls remain in place. Conventional HVAC systems often require an upgrade when additional filter media is introduced into the system. For instance, the additional filter media may put a strain on the function of the circulating fan, which leads to earlier burnout of the fan and/or preemptive replacement of the fan. The fans also consume more energy under this type of strain. As opposed to adding additional filter material as a means to filter unwanted particles from the air system, adding the electro-ionic device 110 described herein into an existing HVAC system 100 has the advantage of minimal strain on the existing components of the system 100.

In certain instances, the HVAC system 100 may be built as-new with electro-ionic device 110 part of the overall system 100. In some instances, as seen in FIG. 1, the HVAC system 100 may also have one or more HEPA filters 106, 112 and the electro-ionic device 110 can be located proximally upwind to at least one of the HEPA filter 112, so that the HEPA filter 112 catches particles which are now subjected to higher levels of ozone to help ensure that there are no viral life particles within the HEPA filter. Effectively, the downstream HEPA filter 112 is sanitized in real time and is unlikely to become a viral reservoir. An ozone sensor 120 may be located just at the outlet vent 122 as this will help with control of the ozone levels within the system 100 itself.

Figure 2:
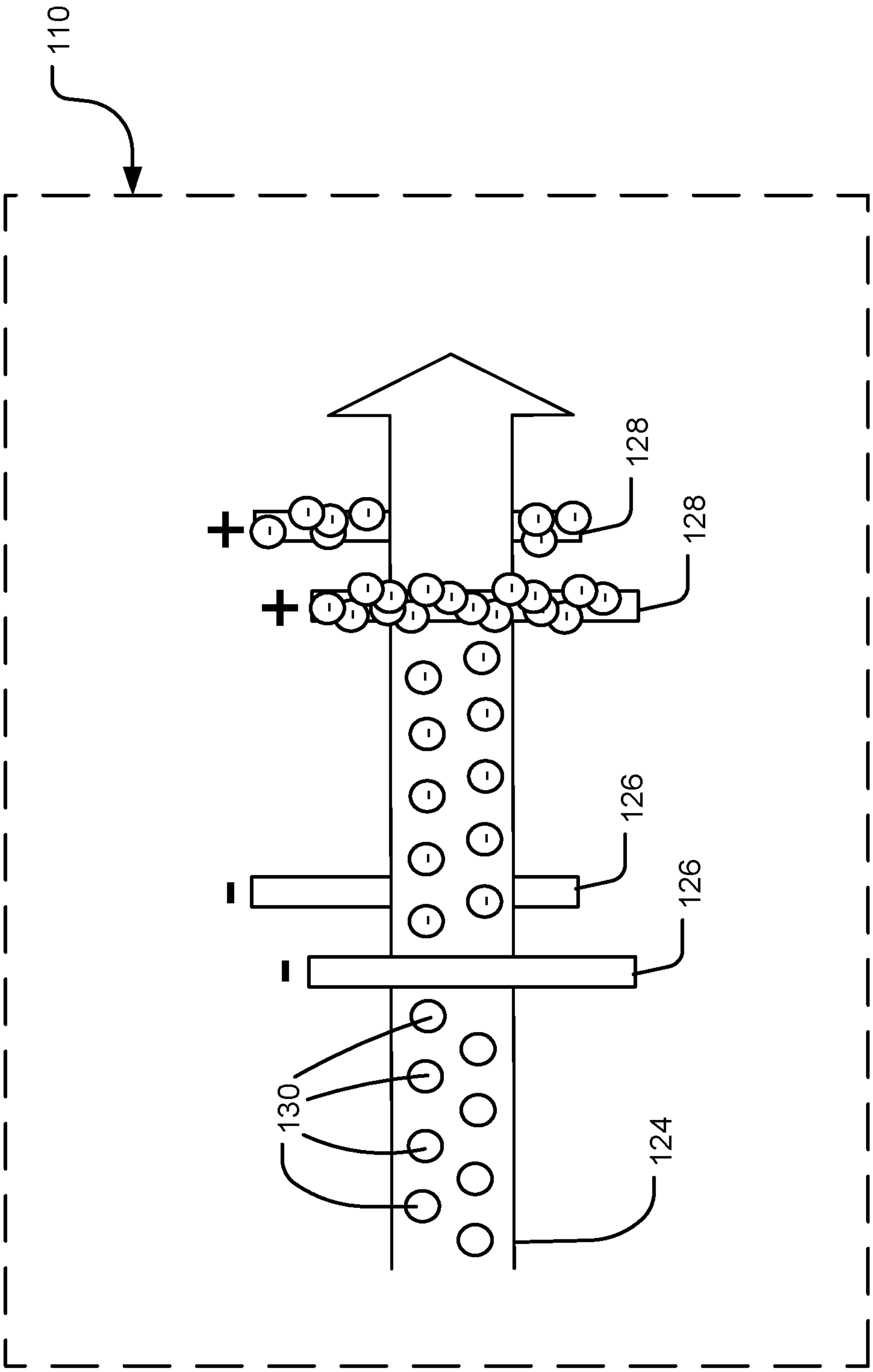
FIG. 2 is a diagrammatic view of the electro-ionic device of FIG. 1.

As seen in the FIG. 2, which is a diagrammatic view of an electro-ionic device 110 with a flow of air 124, the electro-ionic device 110 includes one or more emitters (negative conductor) 126, and one or more collectors (positive conductor) 128. As seen in the figure, there are two emitter 126 posts that are charged with a negative voltage as indicated by the negative sign above each post, and there are two collector 128 posts that are charged positively as indicated by the positive sign above each post. The flow of air 124 generally is representative of fluid flow through a duct of an HVAC system. Within the flow of air 124 are particles 130 such as dust, viral particles, bacterial particles, fungal particles, or the like. The flow of air 124 is left-to-right in FIG. 2. Prior to passing through the emitters 126, the particles 130 are relatively chargeless. Upon passing the emitters 126, the particles 130 pick up a negative charge because of the high negative voltage of the emitters 126, as indicated by the negative sign within the particles 130. Downstream of the emitters 126 are the collectors 128. The negatively charged particles 130 are moving with the flow of air 124 towards and through the collectors 128, which have a high positive charge. The particle 124 are attracted to the positive charge of the collectors 128 and attach themselves on the collectors 128. The air 124 continues to travel past and through the collectors 128 with many of the air particles with foreign matter (e.g., virus particles, bacterial particles, dust, fungus) having been attached to the collectors 128.

In certain instances, the emitters 126 and collectors 128 may be shaped and sized to fit with the ducts of the HVAC system 100 in a way that maximizes ionization of the airflow. The emitters 126 may be formed of stainless steel, or alloys containing nickel, chromium, manganese, combinations thereof, or another oxidation resistant conductive material. The emitter 126 may include various metal foils and/or coats with one or more of the previously mentioned alloys. The emitters 126 may be machined or laser cut into a series of rungs or posts. A portion of the rungs may be coated to help decrease the electron workforce and to improve the efficiency of the electro-ionic device 110. Such coatings may include manganese, iridium, tantalum, and zinc, among others. Reducing the electron workforce may permit a reduction in the emitter voltage and thereby improve the viability of the underlying power source as well as the underlying components.

In operation, a voltage potential is applied between the emitter 126 and the collector plates 128. In certain instances, the voltage potential is −10,000 volts to about −20,000 volts for the emitter 126. With the collector plates 128 being positively charged, this creates an electrostatic precipitator. When the emitter 126 is charged with respect to the collector plates 128, electrons build up on the electrodes of the emitter 126 at their respective tips. Depending on a number of factors, some electrons are transmitted across the gap between the emitter 126 and the collector plates 128. Preferentially, electrons attach to small airborne particles flowing through the duct of the HVAC system and, in particular, though the gap between the emitter 126 and collector plates 128, thereby imparting a negative charge thereto. These charged particles can be precipitated out and/or attracted to the nearby positively charged collector plates 128 creating an inertial diversion.

Figure 3:
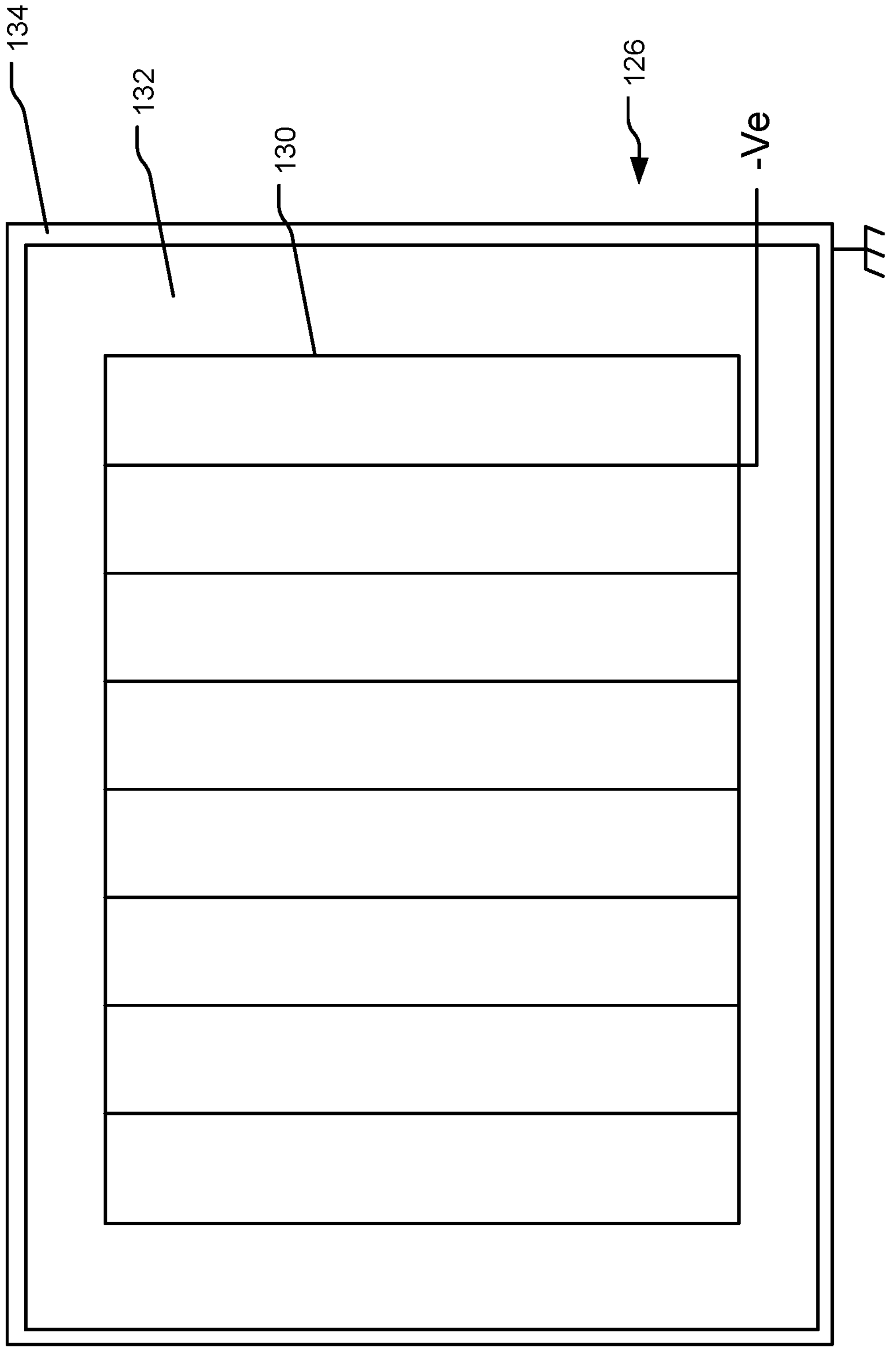
FIG. 3 is a front view of an emitter.

In certain instances, as seen in FIG. 3, which is a front view of an embodiment of the emitter 126 of the electro-ionic device 110, the emitter 126 may include a wire grid or mesh (e.g., conductive mesh) 130 in the form of a series of vertically oriented wires with a rectangular wire frame that encloses the series of vertically oriented wires that are spaced apart from each other so as to permit airflow between the wires. An insulating frame 132 encloses the wire grid 130 on four sides. The frame 132 is enclosed in an outer frame otherwise referred to as a duct frame 134 that extends around the insulating frame 132 on all four sides. The duct frame 134 is sized to fit snugly within the interior space of the duct of the HVAC system. The wire grid 130 is coupled to a voltage source that is configured to supply between about −10,000 volts to about −20,000 volts. The duct frame 134 is grounded to the surrounding ductwork to which it is secured therein.

Figure 4:
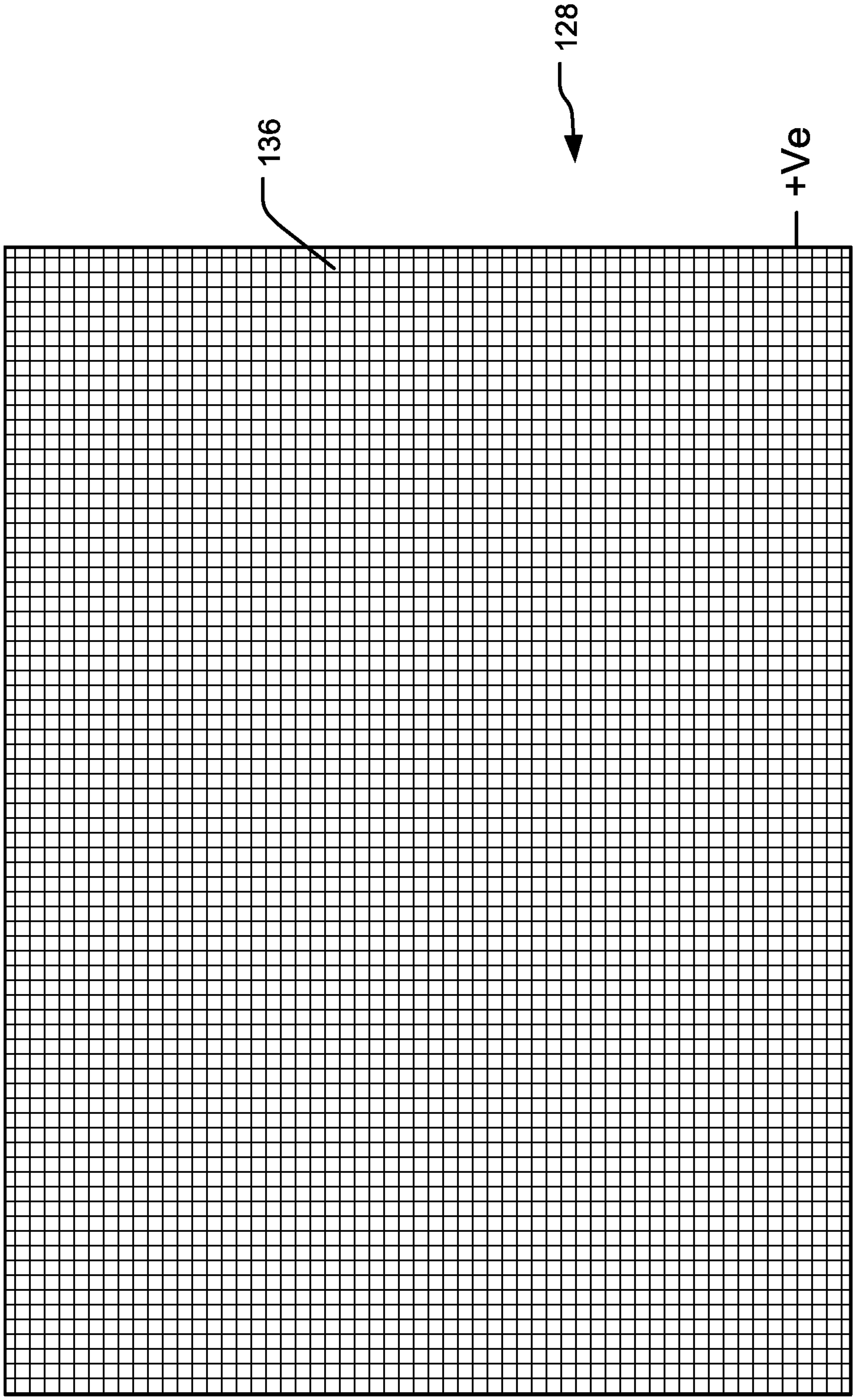
FIG. 4 is a front view of a collector.

FIG. 4 depicts a front view of an embodiment of a collector 128. The collector 128 may include a wire grid 136 in a rectangular shape. In certain instances, a positive voltage charge may be applied to the collector 128 so as to form an electrostatic precipitator. The wire grid 136 is sized to fit within the duct frame 134 shown in FIG. 3. That is, the duct frame 134 is sized to either fit within the existing ductwork or replace a section of ductwork. In the case of replacing a section of ductwork, the existing ductwork could be cut and removed and replaced with the corresponding size of duct frame 134. The duct frame 134 houses the emitter 126 of FIG. 3 and the collector 128 of FIG. 4. In this say, both the emitter 126 and collector 128 span substantially the entire cross-section of the existing ductwork to treat substantially all of the passing airflow.

Figure 5:
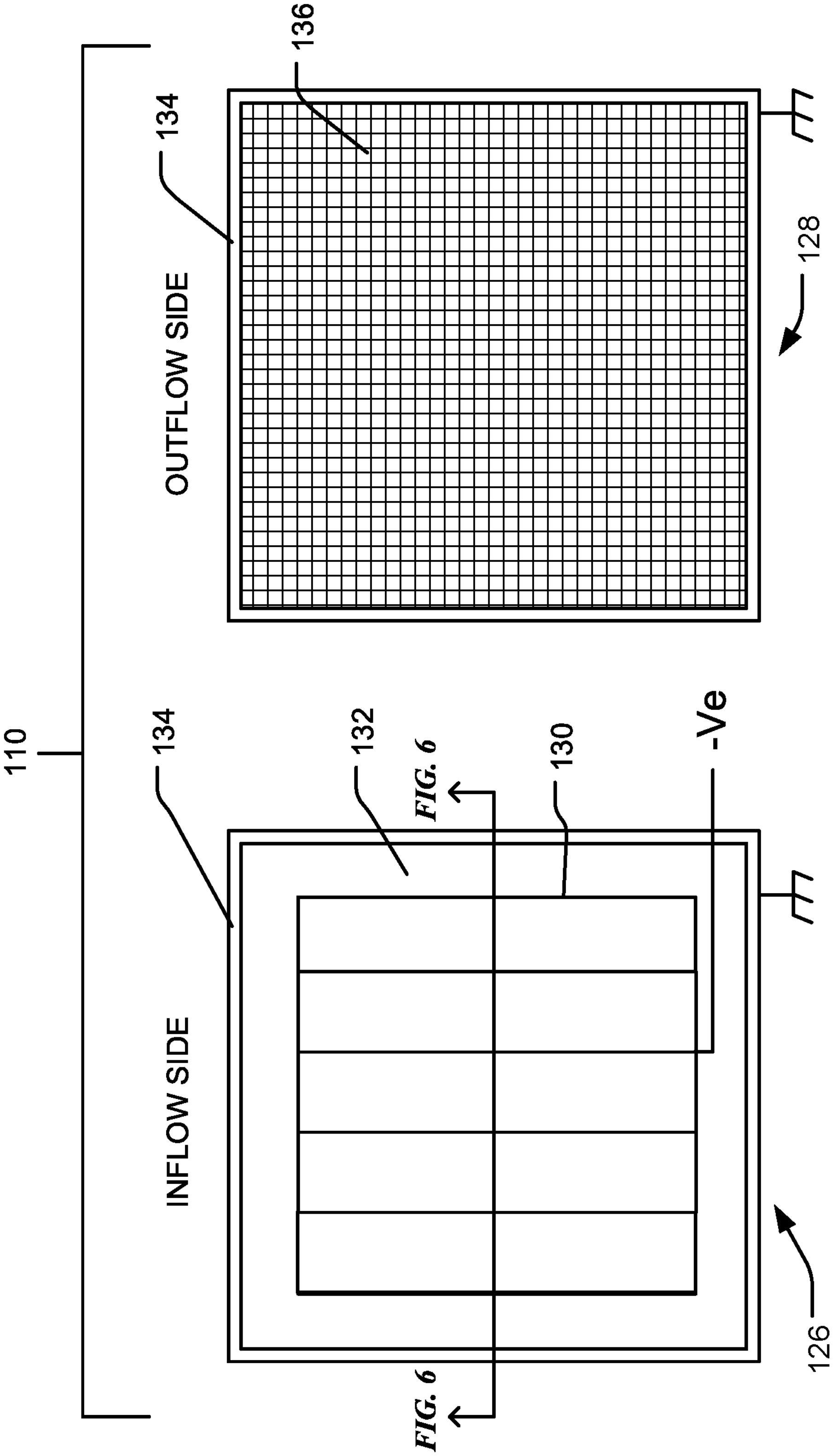
FIG. 5 is an in inflow side view of the electro-ionic device on the left, and an outflow side view of the electro-ionic device on the right.

FIG. 5 shows an embodiment of the electro-ionic device 110 from an inflow side (left) and the outflow side (right). The inflow side depicts the emitter 126 housed within the duct frame 134, and the outflow side depicts the collector 128 housed within the same duct frame 134. The emitter 126 includes the wire grid 130, which is negatively charged, and the insulated frame 132 that encloses the wire grid 130. The duct frame 134 encloses the insulated frame 132. The collector 128 includes the closely spaced wire grid 136.

Figure 6:
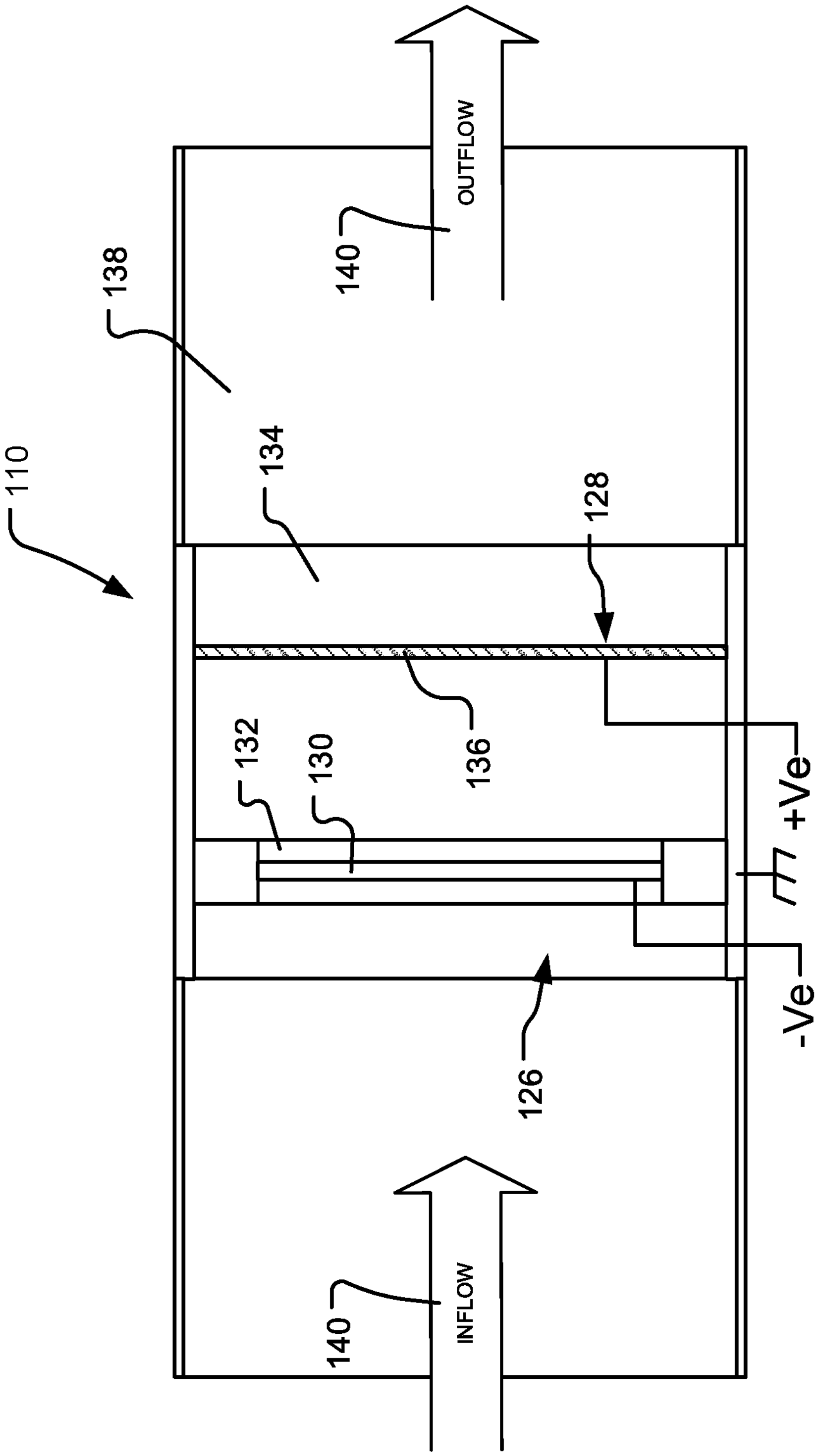
FIG. 6 is a cross-sectional view of the electro-ionic device replacing a section of a duct.

FIG. 6 depicts a cross-sectional view of the electro-ionic device 110 with the section taken at mid-height, as identified by the section-line in FIG. 5 on the left. As seen in FIG. 6, the duct frame 134 in the form of a four sided frame replaces a section of the existing duct 138 of the same size. As seen in FIG. 6, the duct frame 134 is co-extensive with the existing duct 138. Housed within the duct frame 134 is the emitter 126 and the collector 128, both spanning across the entire duct. The emitter 126 includes the wire grid 130 that is housed within the insulating frame 132, which is fitted against the duct frame 134. The wire grid 130 is coupled to a negative voltage. The emitter 126 is upwind of the collector 128 such that the particles within the airflow 140 are negatively charged as it flows through the wire grid 130. The negatively charged particles in the air then flow through the wire grid 136 of the collector 128 and the particles are attracted and collected on the wires of the collector 128. The air continues to flow through the system. In certain instances, the duct(s) of the HVAC system 100 may not include dedicated collector plates 128, but may instead rely at least partially on the ductwork to attract the negatively charged ions. In this way, the electro-ionic device 110 would function as an ion generator.

Control of the electro-ionic device 110 can be exerted both by voltage modulation between the emitter 126 and collector 128 of the electro-ionic device 110 or through duty cycle modulation. For example, at night during absence of the workforce in a given building, the HVAC system 100 may generate higher levels of ozone to significantly sterilize living organisms within the HVAC system itself. This could also be a significant safety mechanism if implemented in airplanes that often circulate air in crowded areas and are often associated with spread of airborne diseases. A secondary control of ozone levels may be implemented near the thermostat accessible living space and may function very much similar to the control applied to temperature. As discussed above, such ozone control can also be integrated with existing temperature and HVAC controls. This may be implemented in a separate ozone control or integrated into an established HVAC control. Ozone level in the air greater than 0.1 ppm may irritate the respiratory tract and may not be conducive to good health. For this reason, the system 100 may implement several ozone sensors to provide better feedback and control for the electro-ionic device 110. Because of the fine control that could be achieved in this manner, higher levels of ozone in the building space may be acceptable when there is absence of people therein. Under such conditions, ozone may disinfect all surfaces, including floors, walls, ceilings, desktops, countertops, etc.

As described above with respect to the electro-ionic device 100, a high voltage positioned in the small gap between the emitter and collector generates high levels of localized ozone by virtue of their discharge. By using this same high voltage in the range of 10 kV to 20 kV and introducing a larger gap between the emitter and collector, such as between 1 to 4 inches, less ozone is produced, but a significant cloud of electrons is emitted. The electrons have a tendency to latch onto small submicron particles and impart a negative charge upon them. In some embodiments, the walls of the ventilation ducts are used as the collector due to their electrical conductivity resulting in a large collector surface area. Accordingly, the device described herein may be used to convert an existing HVAC into an extended electrostatic precipitator that retains small airborne particles, including biopathogens, and prevents their exit into an occupied room. The concurrent use of purging ozone will help ensure that the trapped biopathogens on the collector will be sanitized and the rendered noninfectious.

The additional functionality of an electrostatic precipitator in combination with an ozone generator is described herein. In one embodiment, the electrostatic precipitator device has a width of approximately 5 inches, which lends itself well to position into an existing ventilation system. The device may be positioned in a duct system downwind from the heater and cooling coils and particularly, downwind from the ozone generator, which is located upwind from the heating cooling coils and the standard HVAC filter. There are at least two connections to this unit, one of which is the negative terminal of the high voltage part and is connected to the emitter thin steel wires that crisscross the lumen of the of the HVAC vent. Because of their negative voltage polarity, they have a tendency to emit electrons to a distance of 1 inch to about 3 inches. The collector grid is referenced to electrical ground where the positive terminal of the voltage generator connects and is in continuity with the vent system. Located within the gap between the negatively charged thin wires of the emitter and the collector grid is the high voltage potential that facilitates the emission of electrons. When small particles pass through both grids, they acquire a negative charge. Some of these charged particles will collide with the collector grid and others will pass through becoming attracted to the extensive conductive duct walls and diverted away from the air stream.

The ionizer devices described herein are designed to be easily inserted into the ducts of HVAC systems, in some instances across its shorter cross section. It is designed to accommodate several different duct size profiles by virtue of midpoint positioning adjustability and emitter voltage adjustability. To accommodate different capacity HVAC systems, basic capacity units may be provided for systems that serve spaces up to 10,000 square feet, such as 5,000 square feet spaces and large capacity units may be provided for systems that serve spaces over 10,000 square feet.

Figure 7:
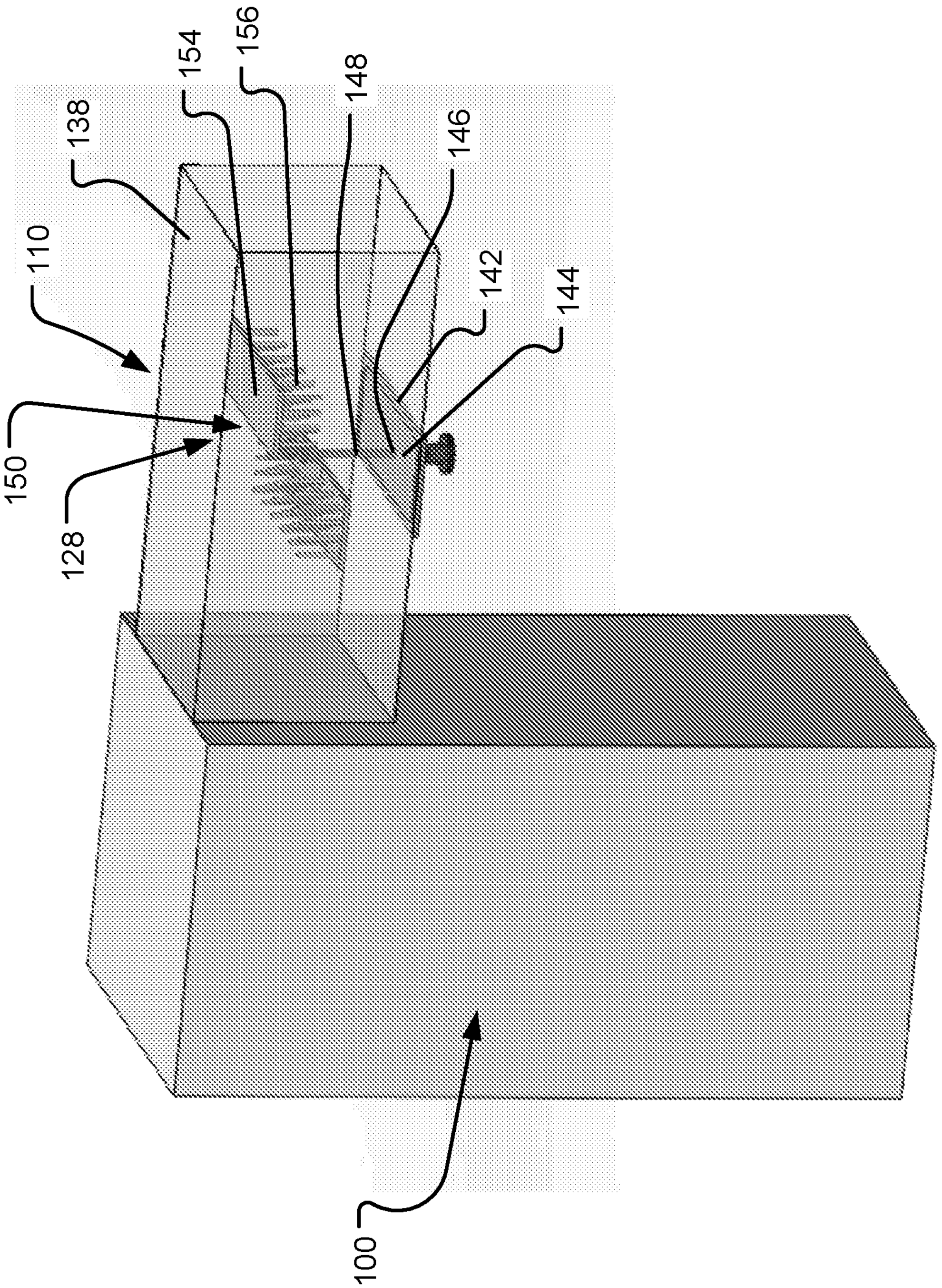
FIG. 7 is an isometric view of an embodiment of the electro-ionic device positioned within a duct.
Figure 8:
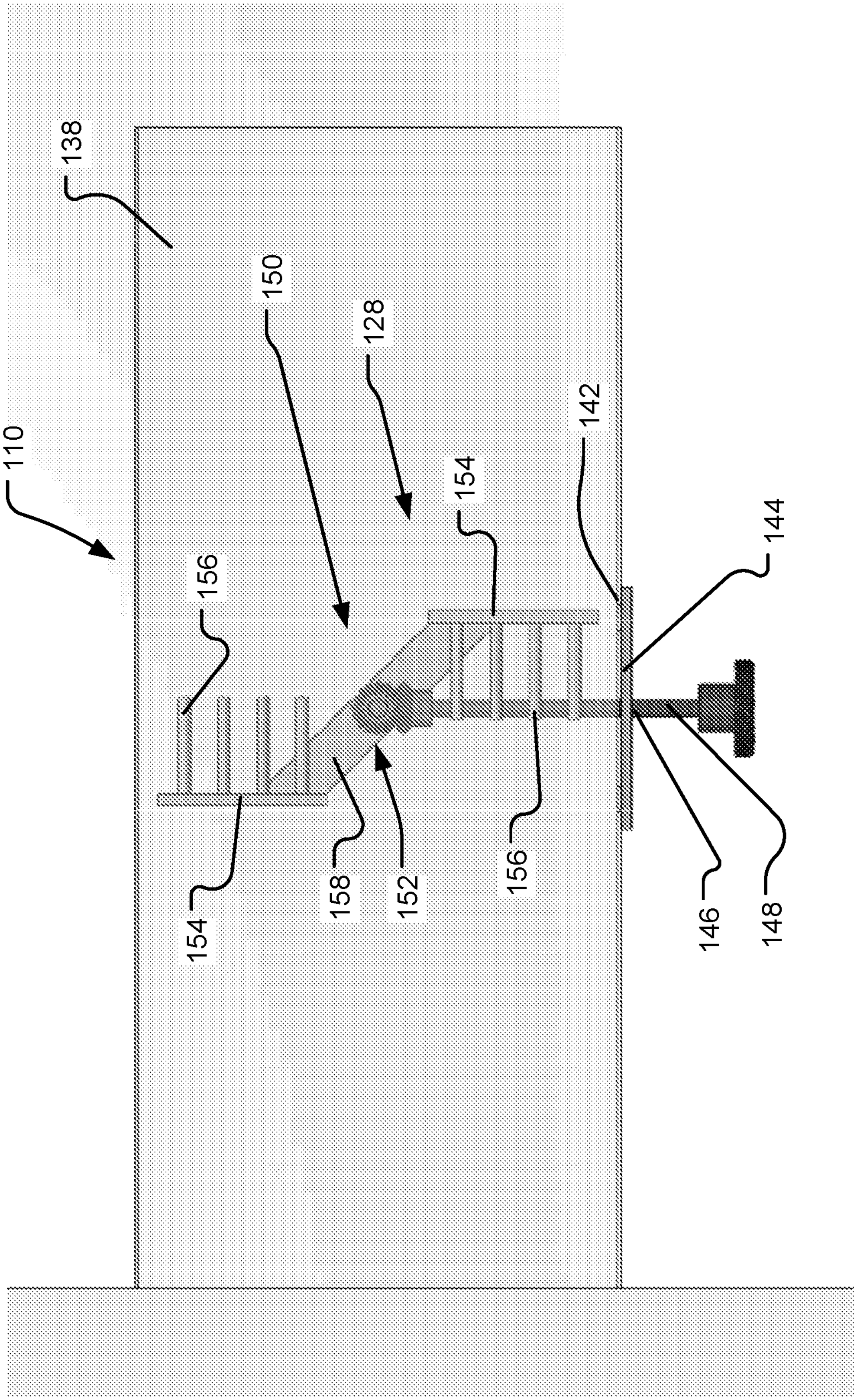
FIG. 8 is a side view of the embodiment of the electro-ionic device of FIG. 7 positioned within a duct and in a non-deployed state.
Figure 9:
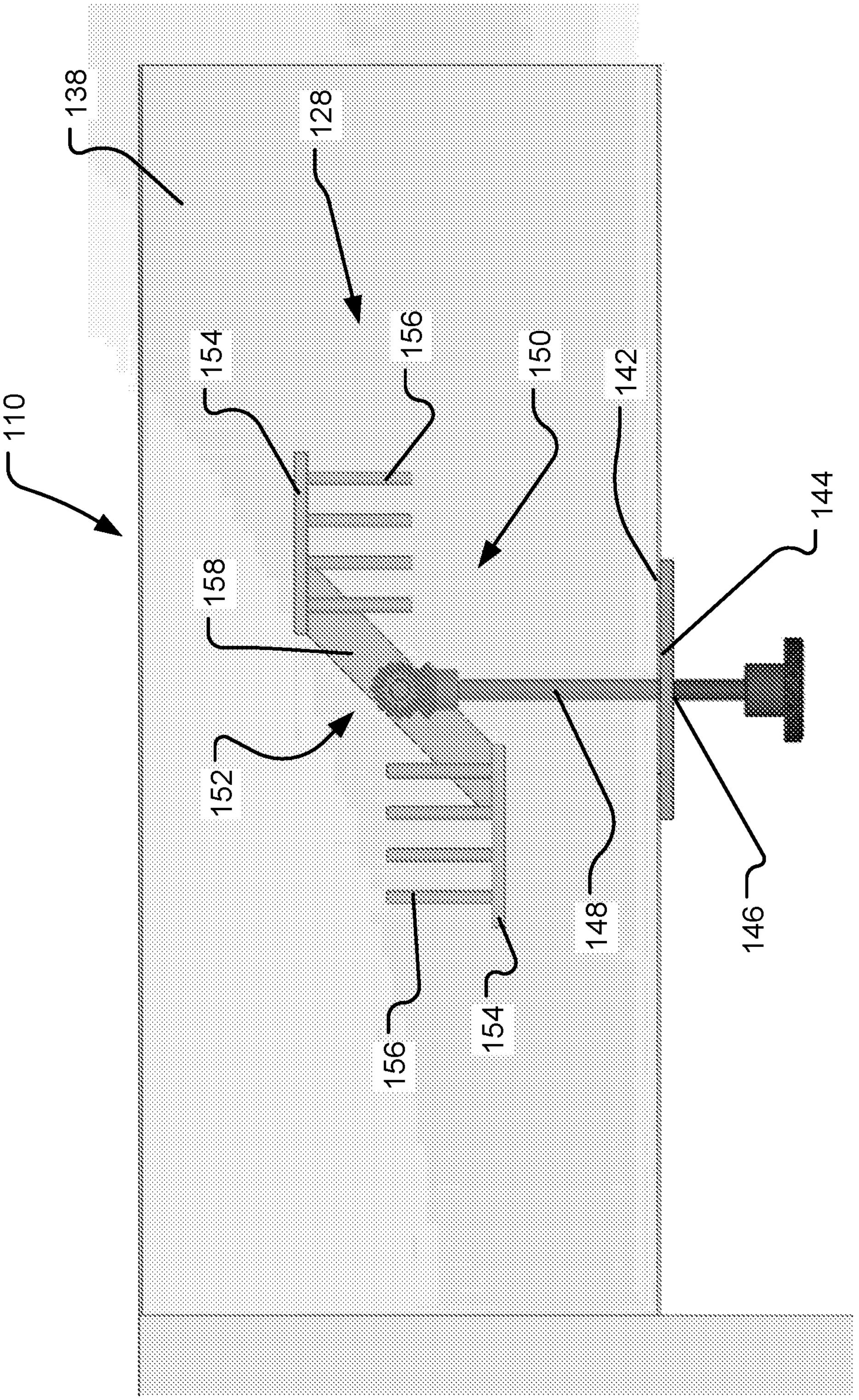
FIG. 9 is a side view of the embodiment of the electro-ionic device of FIG. 7 positioned within a duct and in a deployed state.

In an embodiment as shown in FIGS. 7-9, the electro-ionic device 110 may include an adjustable or deployable emitter 128 that is shown located in a mid-portion of the smaller cross section of a duct 138. FIGS. 7 and 9 show the emitter 128 in a deployed state, whereas FIG. 8 shows the emitter 128 in a non-deployed state. In the deployed state, shown in FIGS. 7 and 9, the emitters 128 are deployed horizontally after insertion into the duct 138. In the non-deployed state, shown in FIG. 8, the emitters 128 are vertical so as to permit insertion of the emitters 128 into an opening (e.g., square cutout) 142 in the duct 138. The deployable nature of the device 110 permits a relatively small opening 142 to be made in the duct 138.

As seen in FIGS. 7-9, the electro-ionic device 110 includes a base plate 144 sized to cover the opening 142 formed into a side of the duct 138. The base plate 144 includes a central opening 146 with an adjustable rod 148 extending there through. The rod 148 is adjustably coupled to an emitter assembly 150 at an end. The rod 148 can be adjusted in height relative to the base plate 144 so as to position the emitter assembly 150 at a particular height within the duct 138, such as at a mid-height within the duct 138. In the illustrated embodiment, the rod 148 is coupled to the emitter assembly 150 via a worm gear assembly 152 (as seen in FIGS. 8 and 9), whereby rotation of the rod 148 about a central axis causes the emitter assembly to transition between the non-deployed and deployed states, as shown in FIGS. 8 and 9, respectively.

The emitter assembly 150 includes a pair of parallel plates 154, each with conductive rods 156 coupled thereto. The plates 154 are rigidly coupled together via a support member 158 in the form of a bar, as seen in FIGS. 8 and 9. The emitter assembly 150 is arranged with the conductive rods 156 cantilevered off of their respective plates 154. The free ends of the rods 156 from one plate 154 opposes the free ends of the rods 156 from the other plate. As seen in FIG. 7, there is a series of rods 156 on the plate 154 that generally spans the surface of the plate 154. In this way, the rods 156 span the width of the duct 138.

In certain instances, the pair of plates 154 may be oriented coplanar with each other. In such an instance, the plates 154 would both be positionable at the midpoint of the duct 138. As seen in FIG. 9, the plate 154 on the left is closer to the lower duct 138, and the plate 154 on the right is closer to the upper duct 138. In order to minimize chances of a short circuit, the device 110 may be modified such that the pair of plates 154 are coplanar such that they both can be positioned at the midpoint of the duct 138 (i.e., equidistant between the upper and lower duct surfaces). In this orientation of coplanar plates 154, the rods 156 may extend in the same direction or opposite directions.

The electro-ionic device 110 may be inserted into the duct 138 in the non-deployed state, as shown in FIG. 8. In this state, the emitter assembly 150 is oriented vertically, with the plates 154 vertical and the rods 156 horizontal. The base plate 144 can be coupled to the duct 138. The rod 148 can be adjusted vertically to center the emitter assembly 150 within the duct 138. The rod 148 can also be adjusted, in this instance by rotation, to rotate the emitter assembly 150 into the deployed state, as shown in FIGS. 7 and 9. In the deployed state, the plates 154 are generally parallel with the upper and lower ducts, as well as with the direction of airflow through the duct 138. And the rods 156 are positioned perpendicular to the flow of air through the duct 138.

The rods 156 of the emitter assembly 150 will have a high voltage negative charge so that electrons emitted from the sharp ends are directed toward the grounded outer walls of the duct system, which are often made from conductive steel or aluminum. High voltage wires may be fitted through the rod 148 or otherwise through the base plate 144. The air space between emitter sharp pointed rods 156 and outer walls of the duct 138 then experiences a significant voltage gradient. As air flows through this voltage gradient space, the particles in the air flow become charge carriers and are thereby attracted and diverted to the duct walls 138, which now have the additional function of acting as an extended collector beyond their original function of containing and directing air flow. In essence, the activation of the electro-ionic device 110 within the duct system of the HVAC system 100 creates an extended electrostatic precipitator.

To further improve efficiency of the ionizer needle emitter, the ends of the rods 156 may be coated with other metals such as zinc, iridium, and/or tantalum to reduce electron emission work force and oxidative corrosion. Additionally or alternatively, the rods 156 may involve coating the sharp projections with carbon nanotubes to improve the efficacy of the emitter 128. Adherence methods for surface coating metals with carbon nanotubes have been optimized for electron emission.

The length of the rods or needles 156 may be in the range of 0.5 centimeters (cm) to 3 cm to accommodate most ducts 138. In certain instances, other lengths are possible. Experimentation revealed that 10 kV works well for particle reduction per 2 cm air gap. In one embodiment, the device 110 uses 40 kV induction on the emitter 128 with 2 cm rods or needles 156 to cover airflow through a duct 138 whose smaller cross section is in the range of 20 cm (8 cm on each side plus 4 cm for needles, 8+8+2+2=20 cm). Because ducts 138 come in different cross sections, the emitter devices described herein are able to be used in different duct cross sections, and are further able to have midpoint positioning adjustability and inductive voltage variability. For most situations, the operational range of the voltage may be between 10 kV and 100 kV. Testing showed that with air gaps of 2 cm and a collector length of 4 cm, >95% particle reduction was achieved with airflows of 30 liters/minute and as high as 80 l/m through the 2 cm gap and 10 kV field gap. Extended collector surface area of the duct system will produce improved particle reduction with higher airflows, a smaller emitter, and lower voltages.

Activation of a purge cycle floods the living space with higher levels of supercharged oxygen (SO). Supercharged oxygen is biologically toxic or at least irritating at levels of 0.2 ppm/2 hours (OSHA standard) or 0.1 ppm/8 hours (OSHA standard for work environments). In a maintain mode of operation, it is intended that the living space level of ozone is maintained below the set level which usually will be below 0.1 ppm and the duct system at higher levels to maintain virucidal activity.

In the purge mode, the operator may set the target SO in the living space and its duration. When the living space is not ventilated with outside air, it was found that the average half-life of residual SO is of the order of 20 minutes. If more rapid degradation is desired, an enhanced external ventilation can be automatically implemented and or catalytic degradation device within the vent system and/or living space can be activated.

For the purge mode, the operator can set the initiation time and duration of purge as well as the maximum oxidant level within the living space to be maintained. A link to existing security system motion detectors may be used as third step in safety activation of our purge cycle with a given space in addition to activation controls.

Figure 10B:
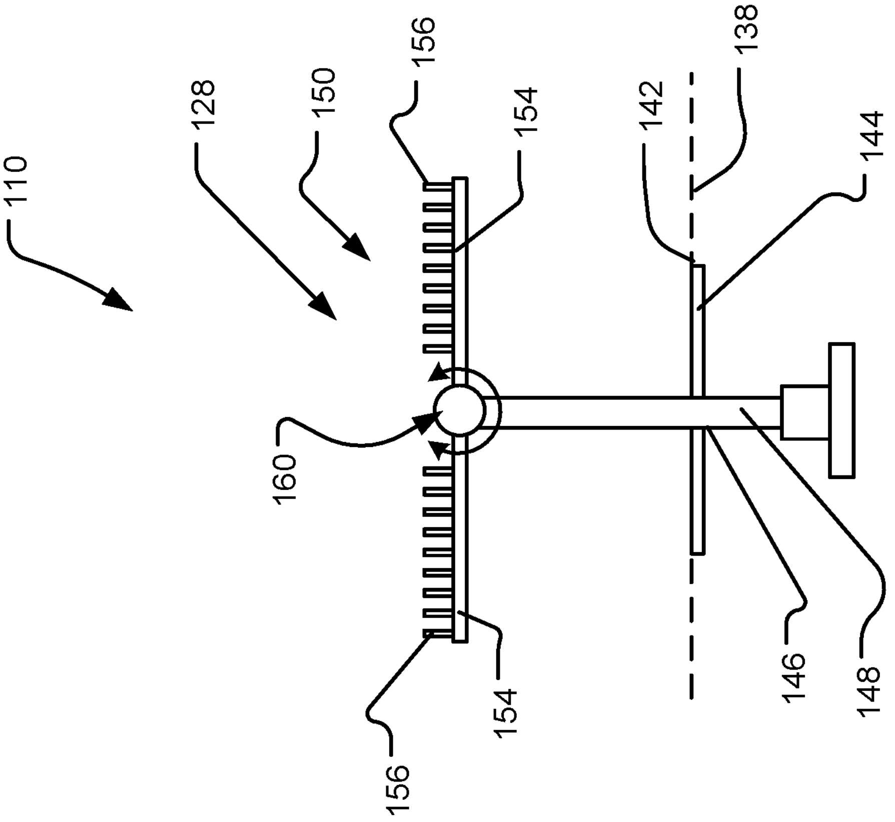
FIGS. 10A and 10B are, respectively, side views of an embodiment of an electro-ionic device positioned within a duct in a non-deployed state, and a deployed state.
Figure 10A:
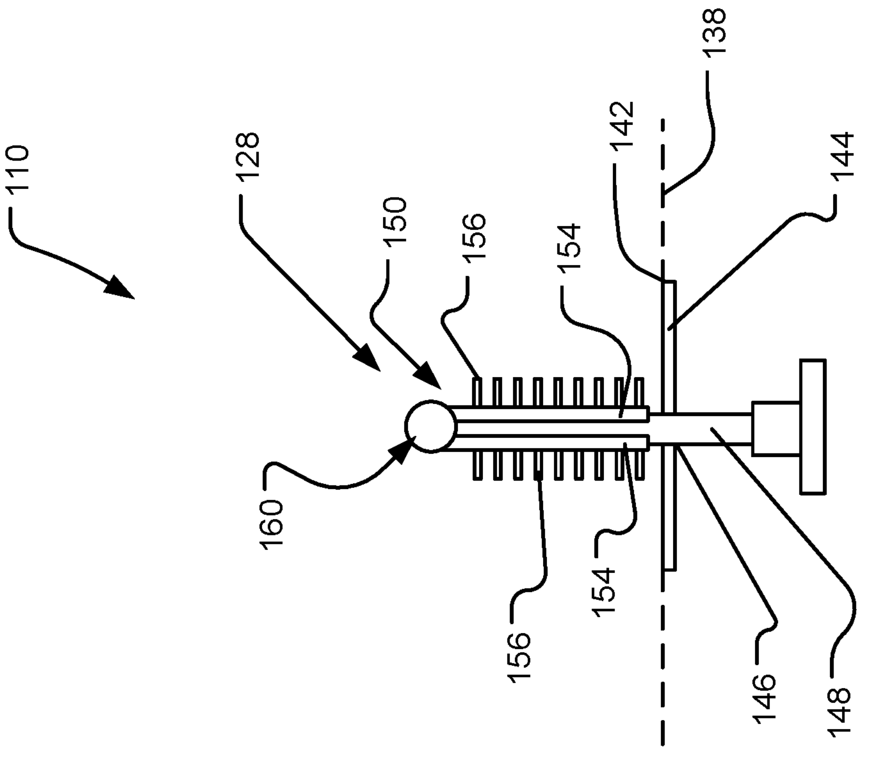

FIGS. 10A and 10B depict, respectively, an embodiment of an electro-ionic device 110 in a non-deployed state, and a deployed state. The electro-ionic device 110 is similar with respect to the device shown in FIGS. 7-9, except the device in FIGS. 10A and 10B includes a pair of plates 154 that are movable relative to each other and are rotatable about a central joint 160. In the non-deployed state of FIG. 10A, the plates 154 are parallel with each other and vertically oriented with the rods 156 extending horizontally in opposite directions. In this way, the width of the emitter assembly 150 is narrower than the base plate 144 and the opening 142 in the duct 138. Once the emitter assembly 150 is inserted into the duct 138, the rod 148 may be used to vertically position and secure in place the height of the emitter assembly 150. Then the rod may be used to deploy the emitter assembly 150 into the deployed state, shown in FIG. 10B. Deployment of the emitter assembly 150 may be similar to the deployment of an umbrella where the rod 156 is pulled relative to emitter assembly 150 and a linkage transitions the emitter assembly 150 from the non-deployed state to the deployed state. In the deployed state, the plates 154 are parallel with each other with the rods pointed vertically in the same direction as each other. It is noted that in a different embodiment, the rods 156 could face in opposite directions, or the rod 156 on both plates could face downward in the deployed state. The embodiment of the electro-ionic device 110 shown in FIGS. 10A and 10B may be utilized in pairs. That is an additional device 110 could be positioned upstream or downstream of the device 110 shown in the figures. The second device could be utilized on the opposing wall of the duct 138. Both devices 110 may be connected to the same voltage source, and the second device may be grounded to the surrounding duct 138.

Figure 11A:
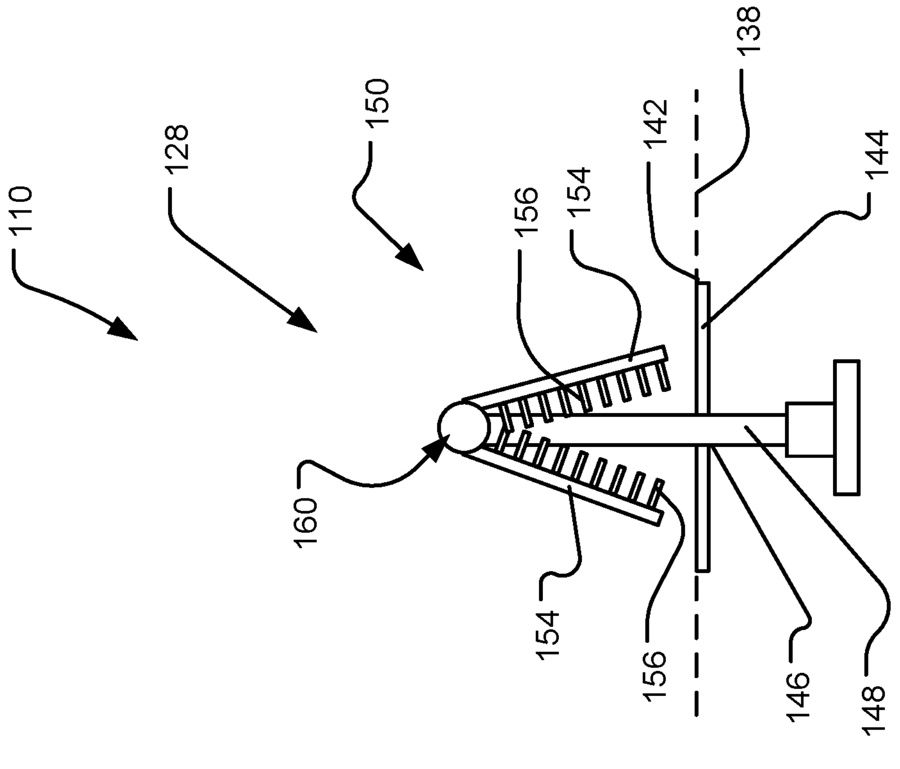
FIGS. 11A and 11B are, respectively, side views of an embodiment of an electro-ionic device positioned within a duct in a non-deployed state, and a deployed state.
Figure 11B:
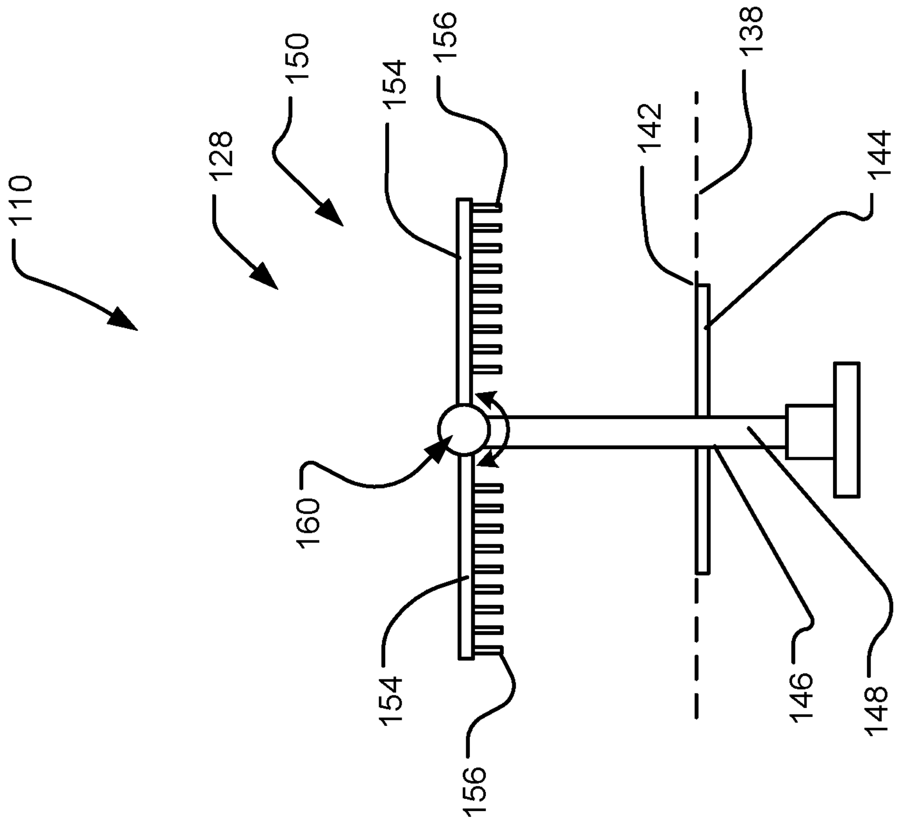

FIGS. 11A and 11B depict, respectively, an embodiment of an electro-ionic device 110 in a non-deployed state, and a deployed state. The electro-ionic device 110 is similar with respect to the device shown in FIGS. 10A and 10B, except the device in FIGS. 11A and 11B includes conductive rods 156 oriented on the opposite sides of the plates 154. In the non-deployed state of FIG. 11A, the plates 154 are angled downward and are rotated inward towards the rod 148. As seen in the figures, the width of the emitter assembly 150 is narrower than the base plate 144 and the opening 142 in the duct 138. Once the emitter assembly 150 is inserted into the duct 138, the rod 148 may be used to vertically position and secure in place the height of the emitter assembly 150. Then the rod may be used to deploy the emitter assembly 150 into the deployed state, shown in FIG. 11B. Deployment of the emitter assembly 150 may be similar to the deployment of an umbrella where the rod 156 is pulled relative to emitter assembly 150 and a linkage transitions the emitter assembly 150 from the non-deployed state to the deployed state. In the deployed state, the plates 154 are parallel, and coplanar with each other. The rods 156 are pointed vertically and positioned on the bottom side of the plates 154. It is noted that in a different embodiment, the rods 156 could face in opposite directions. The embodiment of the electro-ionic device 110 shown in FIGS. 11A and 11B may be utilized in pairs. That is an additional device 110 could be positioned upstream or downstream of the device 110 shown in the figures. The second device could be utilized on the opposing wall of the duct 138. Both devices 110 may be connected to the same voltage source, and the second device may be grounded to the surrounding duct 138.

Figure 12A:
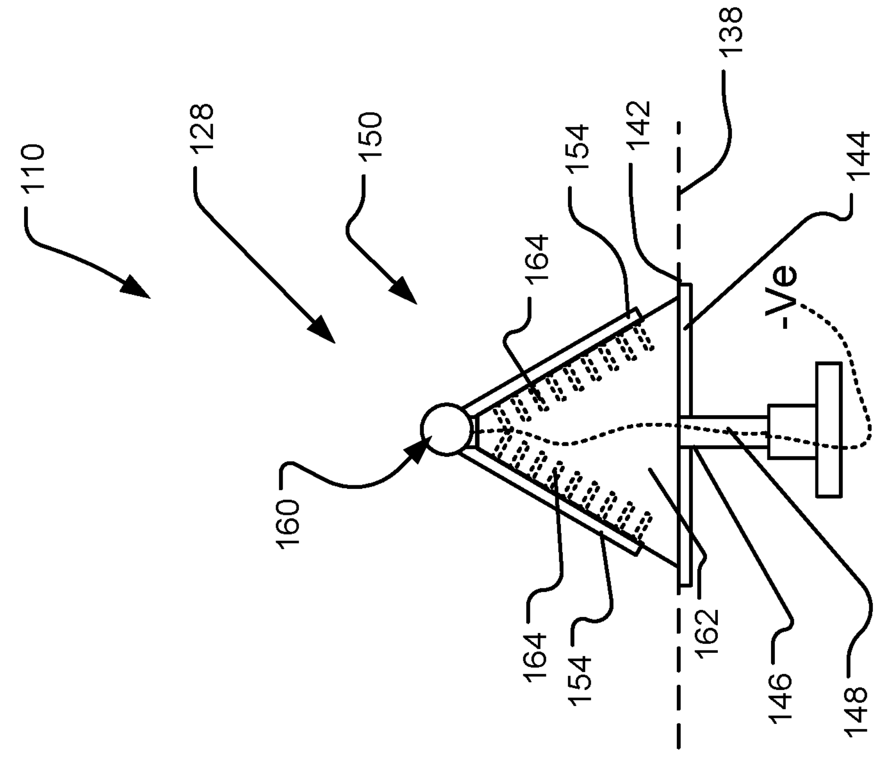
FIGS. 12A and 12B are, respectively, side views of an embodiment of an electro-ionic device positioned within a duct in a non-deployed state, and a deployed state.
Figure 12B:
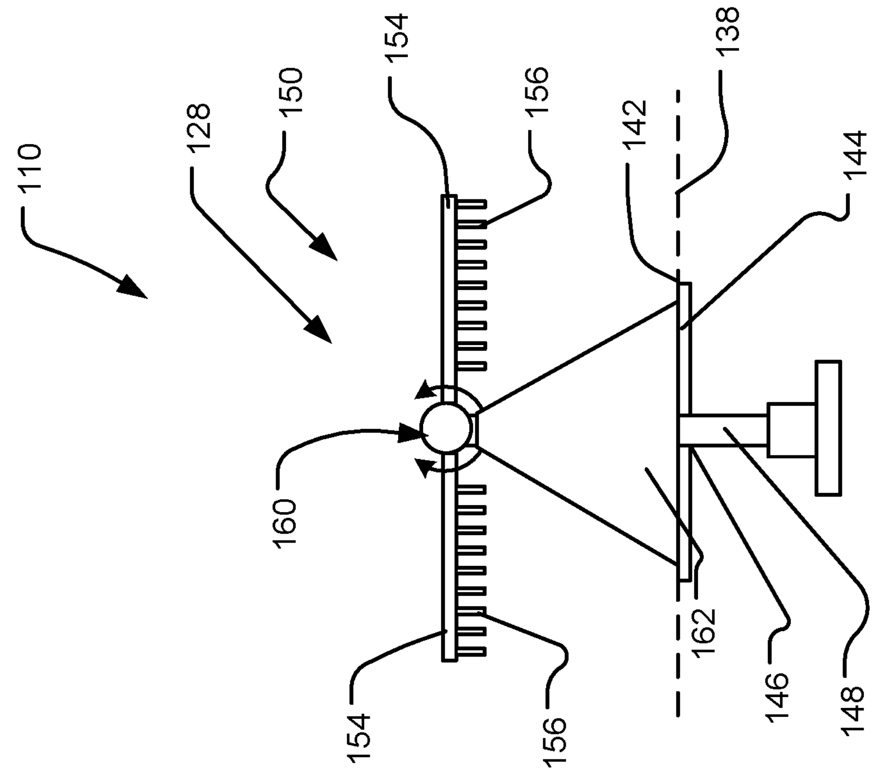

FIGS. 12A and 12B depict, respectively, an embodiment of an electro-ionic device 110 in a non-deployed state, and a deployed state. The electro-ionic device 110 is similar with respect to the device shown in FIGS. 11A and 11B, except the device in FIGS. 12A and 12B includes a base platform 162 positioned on the base plate 144 that includes recesses 164 for receiving the rods 156 when the device 110 is in the non-deployed state. As with the device in FIGS. 11A and 11B, there are a pair of plates 154 that are movable relative to each other and are rotatable about a central joint 160. In the non-deployed state of FIG. 12A, the plates 154 are positioned against the base platform 162, which is triangular in shape. In this state, the rods 156 are received within the recesses 164 of the platform 162, which may be constructed of a non-conductive material such as plastic. This protects the rods 156 when not in use (i.e., not in the deployed state). As seen in FIG. 12A, the width of the emitter assembly 150 is narrower than the base plate 144 and the opening 142 in the duct 138. Once the emitter assembly 150 is inserted into the duct 138, the rod 148 may be used to vertically position and secure in place the height of the emitter assembly 150. Then the rod may be used to deploy the emitter assembly 150 into the deployed state, shown in FIG. 12B. Deployment of the emitter assembly 150 may be similar to the deployment of an umbrella where the rod 156 is pulled relative to emitter assembly 150 and a linkage transitions the emitter assembly 150 from the non-deployed state to the deployed state. In the deployed state, the plates 154 are parallel, and coplanar with each other with the rods 156 pointed vertically in the same direction as each other. In this embodiment, the rods are pointed downwards towards the base plate 144. It is noted that in a different embodiment, the rods 156 could face in opposite directions, or the rod 156 on both plates could face upwards in the deployed state, as in the device of FIGS. 10A and 10B. The embodiment of the electro-ionic device 110 shown in FIGS. 12A and 12B may be utilized in pairs. That is an additional device 110 could be positioned upstream or downstream of the device 110 shown in the figures. The second device could be utilized on the opposing wall of the duct 138. Both devices 110 may be connected to the same voltage source, and the second device may be grounded to the surrounding duct 138. FIG. 12A shows in dotted lines how the rods 156 can be electrically connected through the rod 148 to a voltage source. The other embodiments can be similarly connected through the rod 148 or otherwise.

In many of the embodiments described herein, the emitters 128 are positioned at a midpoint within the ducts 138 to avoid a short circuit. When deployed, the rods or needles 156 are in a vertical orientation, parallel to the sidewalls of the ducts 138. The rods or needles 156 are also oriented in a perpendicular direction at least one duct wall 138 that acts as a collector wall. With proper application of high-voltage this essentially becomes the configuration of an ionizer with a monopolar emitter 128 and collector configuration (duct wall). In certain instances, to fully cover the cross-section of the duct 138 using devices 110 with midpoint deployment of a monopolar device, a second device 110 can be deployed from the contralateral side and with the needle orientation being against the other wall.

Another aspect of the present disclosure is an ozone generator 200 for use with an HVAC system 100. The ozone generator 200 may be part of an ozone system 202 that further includes additional componentry to power, and control the delivery of ozone through the HVAC system 100. The ozone system 202 may be used with the electro-ionic device 110, or it may be a standalone unit. The ozone generator 200 may connect to an existing HVAC system 100 and functions to kill viruses, fungi, and bacteria in the ductwork and the space the HVAC system 100 is serving. Whereas the electro-ionic device 110 functions to capture the viral and bacterial particles and move them out of the airspace, for example, the ozone generator 200 functions to kill the viral and bacterial products. When used together, the particles are captured, and killed.

The ozone generator 200 may generate ozone, inject it into the ductwork of the HVAC system 100, and circulate the ozone throughout the ductwork and room/building. The system 202 may monitor ozone levels in both the HVAC system and room/building via sensors and be able to control the generation of ozone based on feedback of ozone levels. The system 202 may be connected to a data logger or memory device, such as a computer, to allow for monitoring and logging of system parameters.

Figure 13:
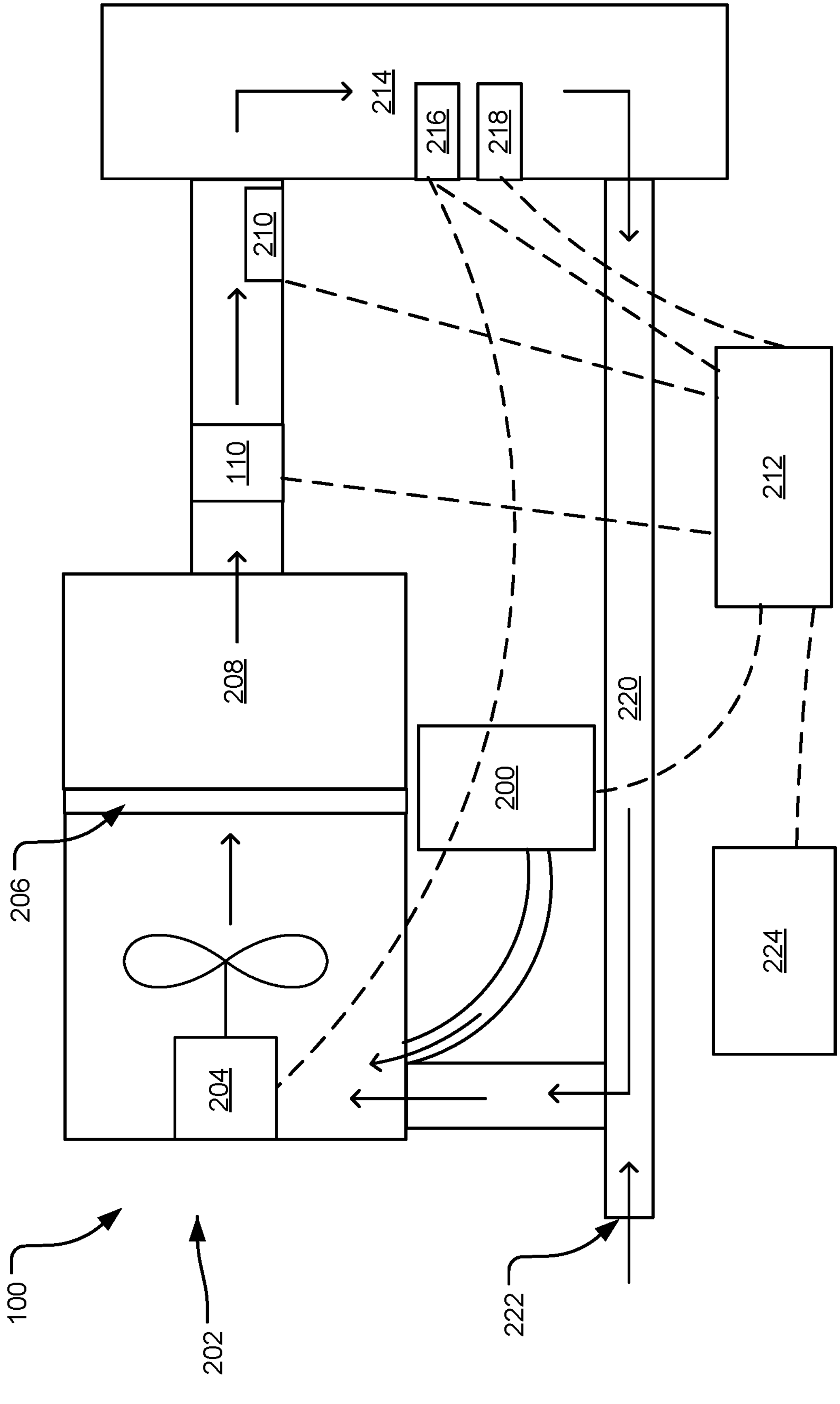
FIG. 13 is a schematic view of an HVAC system integrated with an ozone system and an electro-ionic device.

A schematic of the ozone system 202 is shown in FIG. 13. To begin, the ozone generator 200 is in fluid connection with the blower 204 so as to provide ozone to the blower 204 for circulating with existing air in the system 100 and fresh air. The blower 204 circulates the air and ozone mixture through a filter 206 and through a furnace or AC plenum 208. The air and ozone mixture goes through ducts and may pass through an electro-ionic device 110 as described previously. The electro-ionic device 110 is in communication with a controller 212. In certain instances, there is no electro-ionic device 110. Within the duct, is a supercharged oxygen (SO) sensor 210 that measures SO levels within the duct. The SO sensor 210 is in communication with the controller 212. This sensor is located just prior to the living or working space 214. Within the living space 214 is a thermostat 216 that is in communication with the blower 204 and the controller 212. There is also a second SO sensor 218 located in the living space 214 that is in communication with the controller 212. The living space 214 is in fluid communication with a return duct 220. The return duct 220 routes the conditioned air back to the blower 204 and is also met with a fresh air vent 222. The fresh air, conditioned air, and newly generated ozone are input into the blower for continued circulation. The ozone generator 200 is in communication with the controller 212. And the controller 212 is also in communication with a data logger 224. The arrows in FIG. 13 depict the direction of air and ozone flow through the system 202.

The controller 212 may include a computer and a panel mounted to the HVAC duct near the furnace, upstream from the HVAC filter. The controller 212 may include a user interface, such as a button that allows the user to change operation modes and a display screen or other visible indicators showing operation mode and ozone levels. The controller may control the ozone generator 200, blower 204, and the humidifier (not shown).

The various communications lines indicated by dotted lines in FIG. 13 may be hard lines or wireless communications. There may be a primary wireless unit in the living space 214. This unit may be in communication with the ozone sensor 218 and may communicate with the controller 212 and/or other components. It may contain a display screen or other visible indicators showing operation mode and ozone levels and an audio alarm to alert occupants to high ozone levels. It may contain a key for activating the various modes of operation described subsequently.

The system may be able to operate in three exemplary operation modes: off; maintenance; and purge. In the Off mode, the system 202 will not generate ozone or interact with the HVAC system 100 but will continue monitoring ozone levels. In Maintenance mode, the system 202 produces safe levels of ozone when people are present in the living space. The system will maintain a user set ozone level, such as not to exceed 0.1 ppm average over 24 hrs. Purge mode can produce high levels of ozone intended to disinfect surfaces and is not intended to be used when people are present. Purge mode may be utilized when the air and surfaces in the living space are desired to be sanitized.

Supercharged oxygen is an encompassing term that describes oxidative injury to COVID19 viral particles. It encompasses O3, —OH, H2O2 molecules which are generated concurrently when oxygen and water are subjected to UV light, plasma emission, high voltage gradient and variety of energy sources that can move and dislodge electrons from their usual low energy state. Differentiating peroxide gas, from ozone, from hydroxide is a matter of nomenclature and often used to circumvent regulatory constraints because any molecule that can kill a virus can be irritating and toxic at higher concentrations to living tissue such as lung if inhaled. Oxidizing surface proteins by virtue of dislodged electrons originating in the oxygen molecule whether the oxygen originates as O2 or as H2O is the underlying mechanism for the desired virucidal effect being implemented herein within the HVAC system. The system described herein may also activate existing HVAC humidifier function to increase water vapor presence which improves virucidal efficacy. With water a greater fraction of supercharged oxygen is in the form of gas hydrogen peroxide and as such exhibits less irritation to respiratory system than equivalent ozone levels in the absence of water vapor.

By combining this ionizer 110 with the ozone generator 200, along with a feedback control circuit, a significant particle reduction and neutralization is possible for existing circulating biologicals that potentially can cause harm by virtue of them being airborne bio pathogens. The technology herein accomplishes what prior devices have struggled to is not only particle enhance particle reduction but also virucidal and bio pathogen reductions in real time without significant modification of existing HVAC systems.

Figure 14:
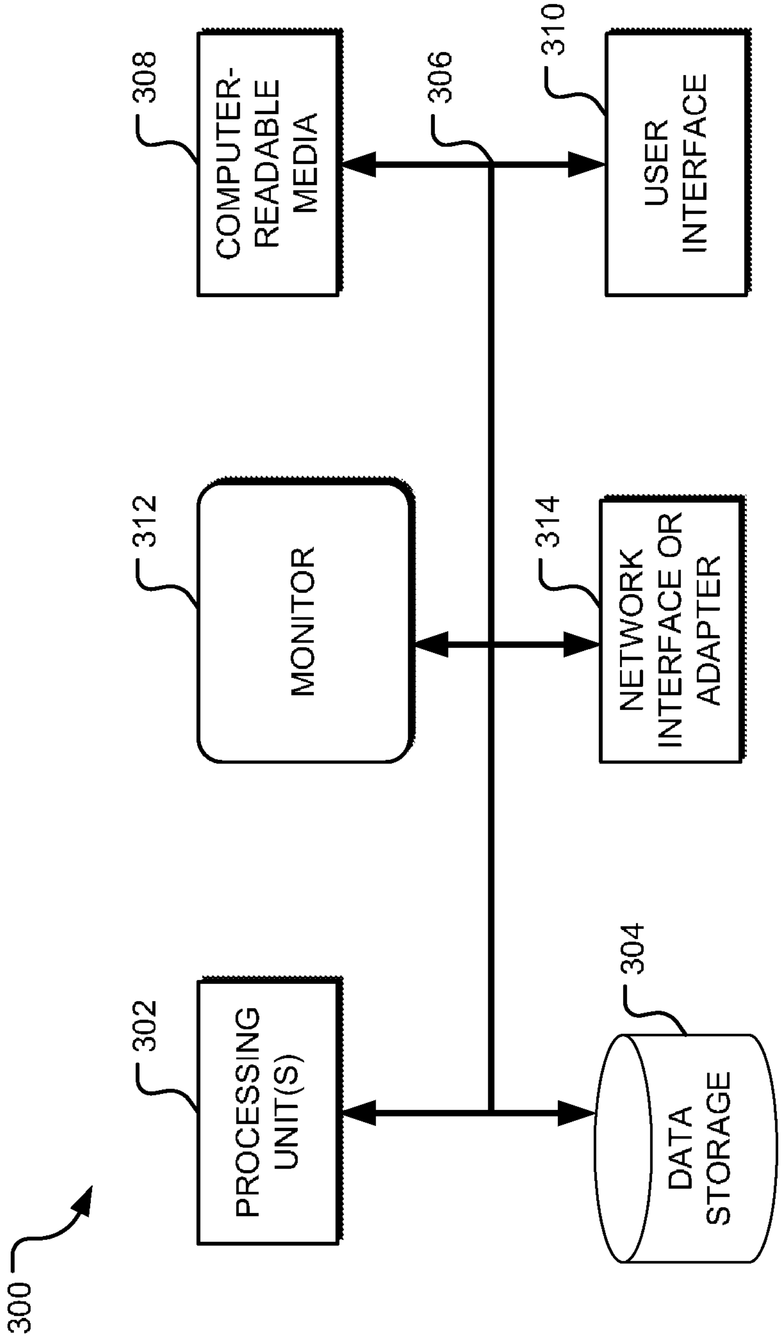
FIG. 14 is a schematic of a suitable computing and networking environment that may be used to implement various aspects of the present disclosure.

FIG. 14 illustrates an example of a suitable computing and networking environment 300 that may be used to implement various aspects of the present disclosure described in FIG. 14, among others. As illustrated, the computing and networking environment 300 includes a general purpose computing device 300 capable of operating the functions of the data logger, and/or the controller in FIG. 14, although it is contemplated that the networking environment 300 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 300 may include various hardware components, such as a processing unit 302, a data storage 304 (e.g., a system memory), and a system bus 306 that couples various system components of the computer 300 to the processing unit 302. The system bus 306 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 300 may further include a variety of computer-readable media 308 that includes removable/non-removable media and volatile/nonvolatile media, but excludes transitory propagated signals. Computer-readable media 308 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/ data and which may be accessed by the computer 300. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 304 includes computer storage media in the form of volatile/nonvolatile memory such as read only memory (ROM) and random access memory (RAM). A basic input/output system (BIOS), containing the basic routines that help to transfer information between elements within the computer 300 (e.g., during start-up) is typically stored in ROM. RAM typically contains data and/or program modules that are immediately accessible to and/or presently being operated on by processing unit 302. For example, in one embodiment, data storage 304 holds an operating system, application programs, and other program modules and program data.

Data storage 304 may also include other removable/non-removable, volatile/nonvolatile computer storage media. For example, data storage 304 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 14, provide storage of computer-readable instructions, data structures, program modules and other data for the computer 300.

A user may enter commands and information through a user interface 310 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 302 through a user interface 310 that is coupled to the system bus 306, but may be connected by other interface and bus structures, such as a parallel port, game port or a universal serial bus (USB). A monitor 312 or other type of display device is also connected to the system bus 306 via an interface, such as a video interface. The monitor 312 may also be integrated with a touch-screen panel or the like.

The computer 300 may operate in a networked or cloud-computing environment using logical connections of a network interface or adapter 314 to one or more remote devices, such as a remote computer. The remote computer may be a personal computer, a server, a router, a network PC, a peer device or other common network node, and typically includes many or all of the elements described above relative to the computer 300. The logical connections depicted in FIG. 14 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 300 may be connected to a public and/or private network through the network interface or adapter 314. In such embodiments, a modem or other means for establishing communications over the network is connected to the system bus 306 via the network interface or adapter 314 or other appropriate mechanism. A wireless networking component including an interface and antenna may be coupled through a suitable device such as an access point or peer computer to a network. In a networked environment, program modules depicted relative to the computer 300, or portions thereof, may be stored in the remote memory storage device.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for mitigation of environmental loading of biopathogens, the system comprising:

an electro-ionic device in fluid communication with ducts of an airflow system and configured to ionize airflow within the ducts, the electro-ionic device including an emitter insulated from contact with the ducts and configured to be supplied with a negative voltage, and at least one collector configured to be supplied with a positive voltage;

an ozone generator apart from the electro-ionic device, the ozone generator in fluid communication with the ducts and configured to deliver ozone into the airflow within the ducts upwind from the electro-ionic device;

a controller in communication with and configured to control the electro-ionic device and the ozone generator; and at least one ozone sensor configured to detect levels of ozone in an area, the at least one ozone sensor in communication with the controller, wherein the emitter and the at least one collector are each in the form of a wire grid.

2. The system of claim 1, wherein the at least one collector is disposed in close proximity to the emitter the at least one collector being grounded to the ducts, the electro-ionic device being an electrostatic precipitator.

3. The system of claim 1, further comprising a humidifier in fluid communication with the ducts and in communication with the controller.

4. The system of claim 1, wherein the at least one ozone sensor comprises a first ozone sensor and a second ozone sensor, the first ozone sensor positioned within the ducts, and the second ozone sensor positioned outside the ducts.

5. The system of claim 1, wherein the controller is configured to maintain ozone within the ducts at an average level that is greater than 0.1 parts per million.

6. The system of claim 1, wherein the controller is configured to decrease an amount of ozone delivered into the ducts by the ozone generator when a threshold value of ozone is exceeded as detected by the at least one ozone sensor.

7. The system of claim 1, wherein the delivery of the ozone into the ducts is configured to kill at least a portion of the biopathogens within the ducts, wherein the controller is configured to maintain ozone within a living space at an average level that is less than 0.1 parts per million.

8. The system of claim 1, wherein the at least one ozone sensor comprises a first ozone sensor positioned at an outlet of the ducts and a second ozone sensor positioned within a living space, the outlet of the ducts being in fluid communication with the living space.

9. The system of claim 1, further comprising a primary unit positioned in a living space and in communication with the at least one ozone sensor, the primary unit configured to communicate an alert when a threshold value of ozone is exceeded at the at least one ozone sensor.

10. The system of claim 1, wherein the emitter is configured to negatively charge the biopathogens and the at least one collectors is configured to attract the biopathogens when the electro-ionic device is ionizing the airflow.

11. The system of claim 1, wherein the at least one collector is configured to be supplied with a positive voltage, wherein the emitter is configured to negatively charge the biopathogens and the at least one collector is configured to attract the biopathogens when the electro-ionic device is ionizing the airflow.

12. The system of claim 1, wherein the ozone generator is located apart from the ducts.

13. The system of claim 1, further comprising a fan in fluid communication with the ducts and in communication with the controller, the fan configured to cause the airflow to flow through the ducts, wherein the controller is configured to activate the fan when the electro-ionic device is activated.

14. The system of claim 1, further comprising at least one coil in fluid communication with the ducts and in communication with the controller, the at least one coil comprising: a heating coil or an expansion coil.

15. The system of claim 1, wherein control of the electro-ionic device is configured to be exerted by voltage modulation between the emitter and the at least one collector.

16. The system of claim 1, further comprising a filter and at least one coil disposed within the ducts, wherein the ozone generator is positioned upstream of both the filter and the at least one coil, the at least one coil comprising: a heating coil or an expansion coil.

17. A system for mitigation of environmental loading of biopathogens, the system comprising:

an electro-ionic device disposed within ducts of an airflow system and configured to capture at least a portion of the biopathogens in airflow within the ducts;

an ozone generator apart from the electro-ionic device, the ozone generator configured to deliver ozone into the airflow within the ducts upwind from the electro-ionic device such that the delivered ozone is capable of killing at least a portion of the biopathogens captured by the electro-ionic device;

a plurality of ozone sensors, each of the plurality of ozone sensors configured to measure levels of ozone in an area; and a controller in communication with the electro-ionic device, the ozone generator, and the plurality of ozone sensors, wherein the electro-ionic device comprises an emitter in the form of a wire grid and configured to be supplied with a negative voltage, and at least one collector in the form of a wire grid and configured to be supplied with a positive voltage.

18. The system of claim 17, wherein the plurality of ozone sensors includes a first ozone sensor within a living space, wherein the controller is configured to adjusts a level of ozone delivered by the ozone generator based on the levels of ozone measured by the first ozone sensor.

19. An ozone system for mitigating environmental loading of biopathogens in ducts of an airflow system, the ozone system comprising:

an ozone generator configured to deliver ozone into the ducts such that at least a portion of the biopathogens is killed in the ducts;

an ozone sensor located in a living space and configured to measure levels of ozone within the living space; and a controller in communication with each of the ozone generator and the ozone sensor, the controller configured to control generation of the ozone when the ozone system is operated in a maintenance mode and in a purge mode, wherein levels of ozone within the living space are higher when the ozone system is operated in the purge mode than when the ozone system is operated in the maintenance mode, and wherein the controller is configured to maintain the levels of ozone within the living space at less than 0.1 parts per million when the ozone system is operated in the maintenance mode.

20. The system of claim 17, wherein the ozone generator is configured to generate an amount of ozone during each of a maintenance mode and a purge mode, wherein the amount of ozone generated during the maintenance mode is less than the amount of ozone generated during the purge mode.

21. The ozone system of claim 19, further comprising an ozone sensor located in the ducts and configured to measure levels of ozone within the ducts, wherein the ozone system is configured to maintain levels of ozone within the ducts at greater than 0.1 parts per million when the ozone system is operated in the maintenance mode.

22. The ozone system of claim 19, wherein the ozone system is configured to be operated in the purge mode when the living space is unoccupied, wherein the controller is in communication with motion detectors for safe activation of the purge mode.

* * * * *